(12) United States Patent
Borchers et al.

(10) Patent No.: US 6,289,107 B1
(45) Date of Patent: *Sep. 11, 2001

(54) APPARATUS AND METHOD OF MEASURING HUMAN EXTREMITIES USING PERIPHERAL ILLUMINATION TECHNIQUES

(75) Inventors: Robert E. Borchers; Joel C. Johnson, both of Lake Oswego; Eric Thomas Peterson, Portland, all of OR (US)

(73) Assignee: Nike, Inc., Beaverton, OR (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/652,350

(22) Filed: May 23, 1996

(51) Int. Cl.[7] ........................................ G06K 9/00
(52) U.S. Cl. .......................... 382/100; 356/391; 600/592
(58) Field of Search ..................... 382/115, 160, 382/100, 123, 128, 174, 203, 211, 260, 264, 266, 283, 312, 199; 356/141.5, 376, 458; 33/3 R, 3 C, 10; 250/559.22; 600/592, 595; 12/146 B; 235/462.43

(56) References Cited

U.S. PATENT DOCUMENTS

| | | | |
|---|---|---|---|
| 4,267,728 | * 5/1981 | Manley et al. ........................ 73/172 |
| 4,315,159 | 2/1982 | Niwa et al. ....................... 250/208.1 |
| 4,419,012 | 12/1983 | Stephenson et al. ............. 356/141.5 |
| 4,604,807 | 8/1986 | Bock et al. ................................ 33/3 |
| 4,672,189 | 6/1987 | Tsunekawa et al. .............. 250/208.1 |
| 4,692,003 | * 9/1987 | Adachi et al. ....................... 351/212 |
| 4,736,203 | * 4/1988 | Sidlauskas ..................... 340/825.34 |
| 4,813,436 | * 3/1989 | Au ........................................ 128/779 |
| 4,858,621 | * 8/1989 | Franks ................................. 128/779 |
| 5,001,557 | 3/1991 | Begle ................................... 348/166 |
| 5,025,476 | 6/1991 | Gould et al. ........................ 382/115 |
| 5,063,603 | * 11/1991 | Burt ..................................... 382/115 |
| 5,128,880 | 7/1992 | White ................................... 364/550 |
| 5,164,793 | 11/1992 | Wolfersberger et al. ............ 356/376 |
| 5,195,030 | 3/1993 | White ................................... 364/401 |
| 5,206,804 | 4/1993 | Thies et al. ......................... 364/401 |
| 5,216,594 | 6/1993 | White et al. ........................ 364/403 |
| 5,237,520 | 8/1993 | White ................................... 364/560 |
| 5,339,252 | 8/1994 | White et al. ........................ 364/468 |
| 5,351,303 | * 9/1994 | Willmore ............................ 382/115 |
| 5,361,133 | 11/1994 | Brown et al. ....................... 356/376 |

(List continued on next page.)

FOREIGN PATENT DOCUMENTS

| | | |
|---|---|---|
| 652 586 A5 | 11/1985 | (CH) . |
| 90/05345 | * 5/1990 | (EP) ..................................... 382/115 |
| 62 248078 A | 10/1987 | (JP) . |
| 05 306995 A | 11/1993 | (JP) . |
| 08 043299 A | 2/1996 | (JP) . |
| 1658995-A1 | 3/1989 | (SU) . |
| WO 90/05345 | 5/1990 | (WO) . |
| WO 94/20020 | 9/1994 | (WO) . |

Primary Examiner—Jayanti K. Patel
(74) Attorney, Agent, or Firm—Banner & Witcoff, Ltd.

(57) ABSTRACT

A device and method is provided for quickly and accurately determining the size and shape of a human extremity such as a foot by projecting light around a periphery of the extremity and capturing an image of the illuminated foot through a transparent plate. Various embodiments contemplate using light having a wavelength in the near-infrared range to reduce contrast problems caused by dyes used in socks and skin tone problems created by highly pigmented individuals. An image of the foot is digitized and stored in a computer memory in both an illuminated state and a non-illuminated state, and the two images are subtracted. Additional image processing steps on the subtracted image result in various measurement quantities such as foot length, width, arch length, heel width, and arch height.

47 Claims, 22 Drawing Sheets

U.S. PATENT DOCUMENTS

| | | | |
|---|---|---|---|
| 5,463,464 | 10/1995 | Ladewski | 356/376 |
| 5,483,601 * | 1/1996 | Faulkner | 382/115 |
| 5,515,268 | 5/1996 | Yoda | 364/401 |
| 5,526,436 * | 6/1996 | Sekiya | 382/115 |
| 5,539,677 | 7/1996 | Smith | 364/560 |
| 5,640,779 | 6/1997 | Rolloff et al. | 33/514.2 |
| 5,732,148 * | 3/1998 | Keagy et al. | 382/124 |
| 5,745,176 * | 4/1998 | Lebens | 348/370 |
| 5,753,931 * | 5/1998 | Borchers et al. | 250/559.22 |
| 5,756,981 * | 5/1998 | Roustaei et al. | 235/462 |
| 5,790,256 | 8/1998 | Brown et al. | 356/376 |
| 5,800,354 * | 9/1998 | Glennie et al. | 600/592 |
| 5,800,364 * | 9/1998 | Glennie et al. | 600/592 |
| 5,983,201 | 11/1999 | Fay | 705/27 |

\* cited by examiner

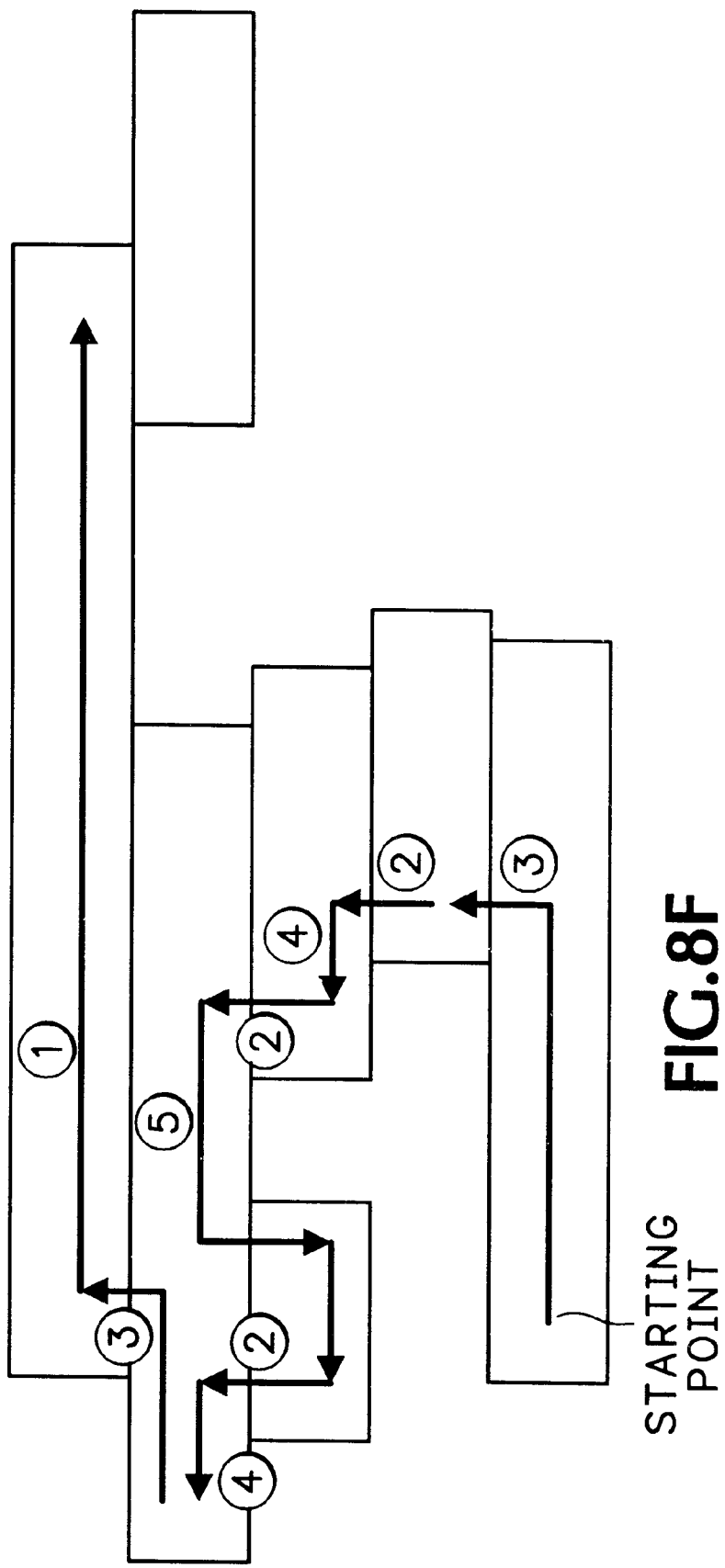

FIG.11B  FIG.11C

APPARATUS AND METHOD OF MEASURING HUMAN EXTREMITIES USING PERIPHERAL ILLUMINATION TECHNIQUES

BACKGROUND OF THE INVENTION

1. Technical Field

This invention relates generally to a computer-controlled device and method for determining the shape and size of a human extremity such as a foot. More particularly, the invention provides foot sizing information by illuminating the periphery of the foot with near-infrared wavelength light and capturing an image of the illuminated foot through a transparent plate.

2. Related Information

There is a need to quickly, accurately, and inexpensively capture detailed information representing the shape and size of a human extremity such as a foot or hand. One application of the invention is the determination of a person's shoe size in a shoe store or other commercial setting. Other applications may include biometric identification of humans based on hand geometry.

Conventional approaches for sizing a human foot have generally required a large number of parts and mechanical structures, many of which may require calibration. As one example, U.S. Pat. No. 5,361,133 to Brown et al. discloses a technique for measuring feet which uses both pressure sensors and infrared LEDs. The device includes two foot-wells each including a pressure sensitive pad and IR diode assemblies. Dozens of circuits are interconnected to receive, convert, and analyze information detected from feet placed into the device.

Another approach disclosed in U.S. Pat. No. 4,604,807 to Bock et al. uses a light source positioned above a foot to project light onto the foot, causing a shadow projection from the foot to be received on a photosensitive array. The shadow projection is used in unspecified algorithms to determine foot size information.

Yet another technique, exemplified by U.S. Pat. No. 5,025,476 to Gould et al., involves projecting a moire fringe pattern through a transparent plate onto the underside of a foot, receiving the image in a computer, and determining foot parameters by calculating distances between various points in the captured image. A special opaque light shield or "sock" is required to prevent ambient light from interfering with the measurements.

The inventors of the present invention have found that conventional approaches for sizing human feet are often inaccurate, expensive, and cumbersome, and are generally unsuitable for use in a large-scale commercial setting such as shoe stores.

SUMMARY OF THE INVENTION

It is one object of the present invention to provide an apparatus and method for measuring human feet or other extremities which is inexpensive yet accurate, and which requires no moving parts.

It is another object of the present invention to provide an apparatus and method for determining the size of a human foot by projecting near-infrared light around the periphery of the foot and receiving an image of the illuminated foot in a computer, wherein the foot may be covered with a person's normal sock (i.e., no special apparel is required).

It is yet another object of the present invention to provide an apparatus and method for measuring a human foot which eliminates the effects of ambient light by subtracting an image of the foot obtained when the foot is illuminated with near-infrared light from an image of the foot when the foot is not illuminated.

It is yet another object of the present invention to provide an inexpensive foot measurement apparatus requiring a minimal number of hardware components.

Other features and advantages of the invention will become apparent with reference to the following detailed description, the accompanying figures, and the appended claims.

BRIEF DESCRIPTION OF THE DRAWINGS

FIG. 8F illustrates graphically the results of using the process shown in FIG. 8e.

FIG. 11B shows various segmented portions of a foot image used to calculate a ratio.

FIG. 11C shows removal of extraneous dark areas from a foot image.

FIG. 12B shows one possible calibration target.

DETAILED DESCRIPTION OF THE PREFERRED EMBODIMENTS

Figure 1:
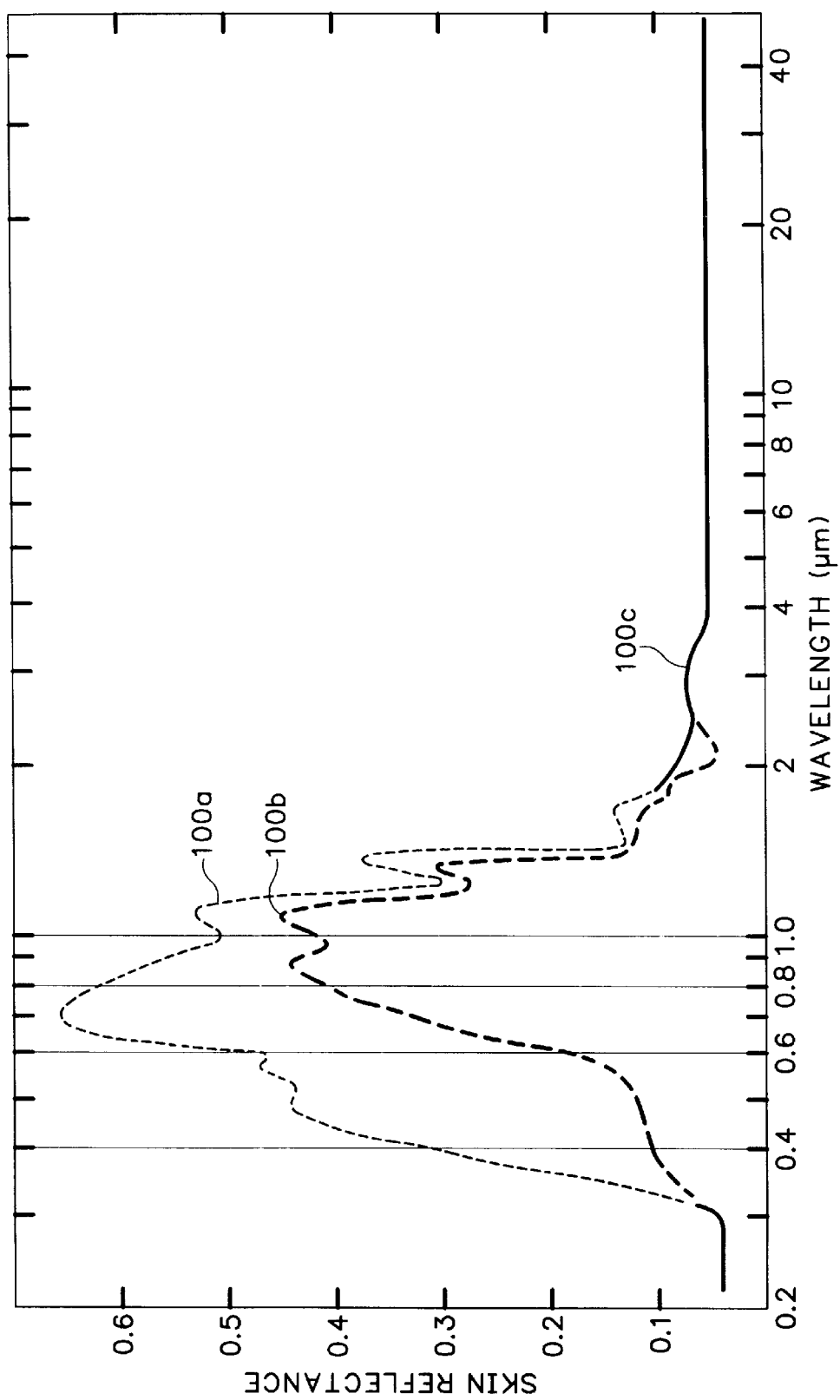
FIG. 1 shows empirical data representing the spectral reflectance of human skin as a function of the wavelength of illuminating light.

FIG. 1 shows empirical data taken from the literature indicating the spectral reflectance of human skin as a function of the wavelength (in micrometers) of illuminating light. Spectral reflectance for persons having a very fair complexion is indicated by function 100a, while reflectance for persons having a heavily pigmented skin is indicated by function 100b. Spectral reflectance for skin in the ultraviolet (UV) and infrared (IR) range is shown by function 100c. While the term "near infrared" can be understood to refer generally to a wavelength range of approximately 0.78 to 3.0 micrometers (780 to 3,000 nanometers), it will be appreciated that the principles of the invention can likely be practiced beyond this specific range. As described in more detail herein, various aspects of the invention contemplate the use of near-infrared light in the 880 nanometer (0.8 micrometer) region for illumination.

Figure 2:
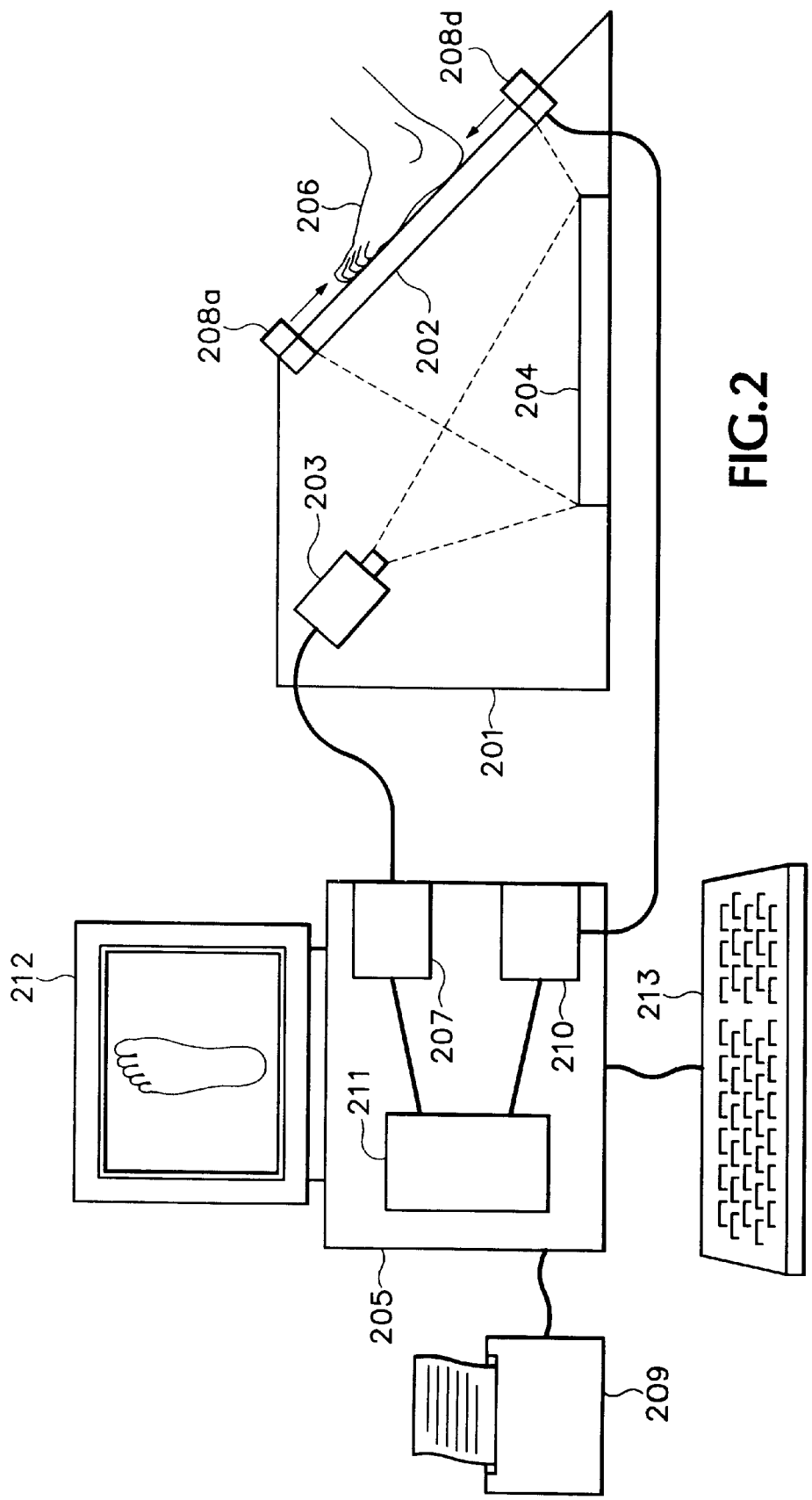
FIG. 2 shows in simplified form a device incorporating various features of the invention including associated control circuitry.

FIG. 2 shows in simplified form a system incorporating various features of the present invention. A housing 201 includes a transparent plate 202 against which a foot or other human extremity 206 is placed. The transparent plate is preferably supported by the housing 201. A camera 203 is disposed within the housing to receive a reflected image of an illuminated foot 206 by way of a mirror 204 disposed on the bottom of housing 201. Optical illuminators 208a and 208d (only two are shown for clarity) are arranged around the periphery of transparent plate 202 to illuminate foot 206, enabling an image of the foot to be formed at camera 203.

A computer 205 includes a frame grabber 207 and an illumination control circuit 210, which are coupled to camera 203 and optical illuminators 208a and 208d respectively. The frame grabber 207 and illumination control circuit 210 can of course be external from the physical computer device with no difference in function or operation. The term "frame grabber" will be understood to refer to any device capable of capturing digital information from a video source. A computer control program 211, described in more detail herein, operates to control frame grabber 207 and optical illuminator control circuit 210 to process reflected images. Instead of a computer-controlled illuminator control circuit, a pushbutton switch or other human-activated device may of course be used. A display device 212 may optionally be included to show a picture of foot 206 as its image is received and processed in computer 205. Additionally, an output device 209 such as a printer may be used to print reports or images of a foot. A keyboard or other input device 213 may be used to allow an operator to control the apparatus.

In accordance with various embodiments of the invention, images of the underside of foot 206 are received in camera 203, captured by frame grabber 207, and processed by computer program 211 operating in computer 205.

It should be noted that the principles of the present invention can be applied to extremities other than feet, such as a hand, head, neck, leg, arm, or even a face, for example. Such applications could include, but are not limited to, determining size information for clothing, and for biometric identification purposes.

Figure 3:
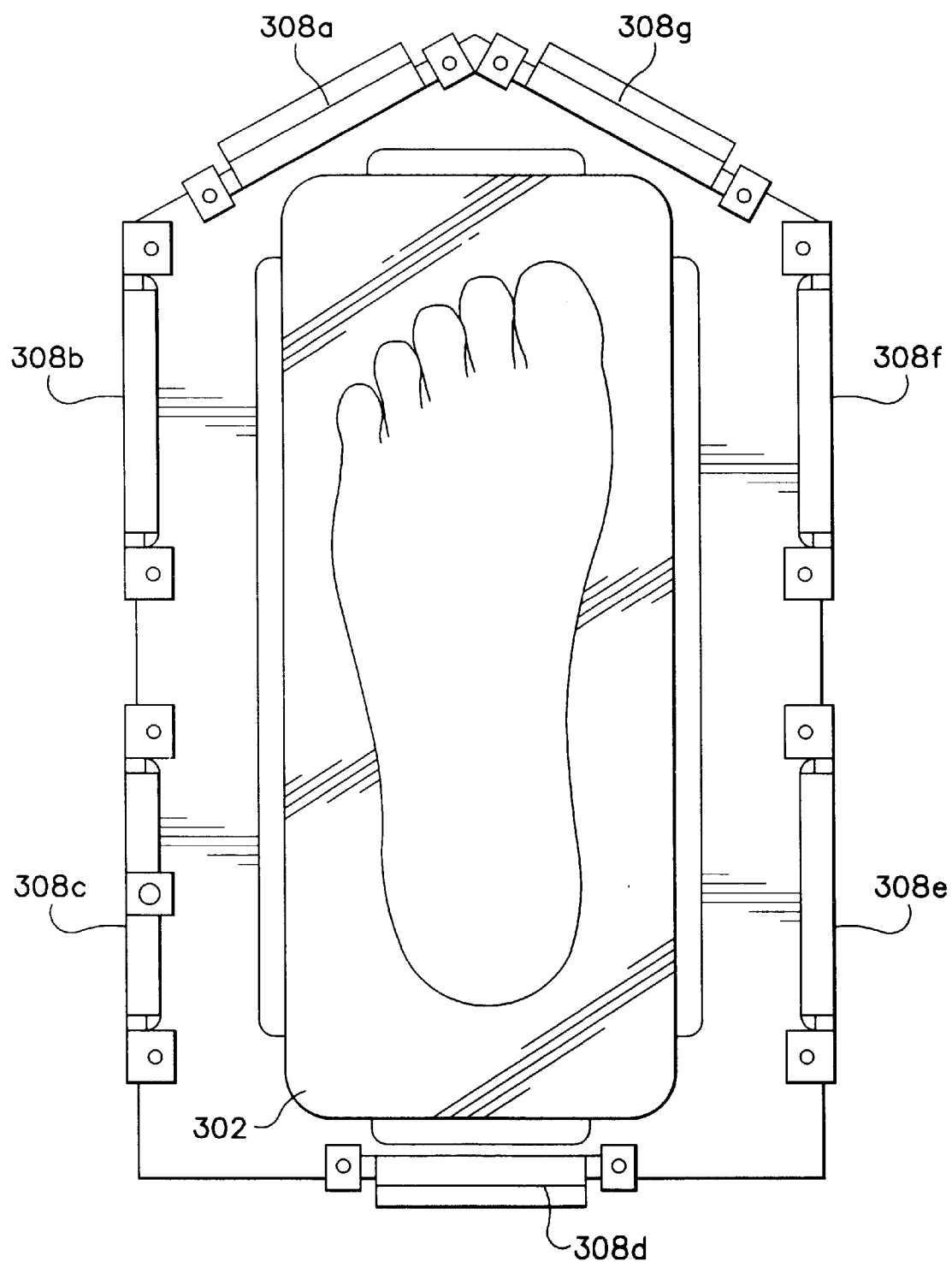
FIG. 3 shows a bottom view of a foot placed on a transparent plate 302 having side illuminators arranged around the periphery of the transparent plate.

FIG. 3 shows a bottom view of a foot placed on a transparent plate 302 having side illuminators arranged in accordance with various embodiments of the invention. As shown in FIG. 3, transparent plate 302 is surrounded by a plurality of optical illumination assemblies 308a through 308g. In particular, two toe illuminators 308a and 308g, two left side illuminators 308b and 308c, a heel illuminator 308d, and two right side illuminators 308e and 308f are arranged around the periphery (not necessarily the edge) of transparent plate 302. A human foot or other extremity may be placed on transparent plate 302 such that its periphery is illuminated when the optical illuminators are activated. It will be appreciated that more or fewer optical illuminators may be used to achieve the intended objects of the invention.

Also, it should be clear that although the optical illuminators are shown spaced apart from the transparent plate, the illuminators could also be located closer to or even on the transparent plate, as long as they are arranged to essentially surround the foot or other object placed on the transparent plate.

Figure 4A:
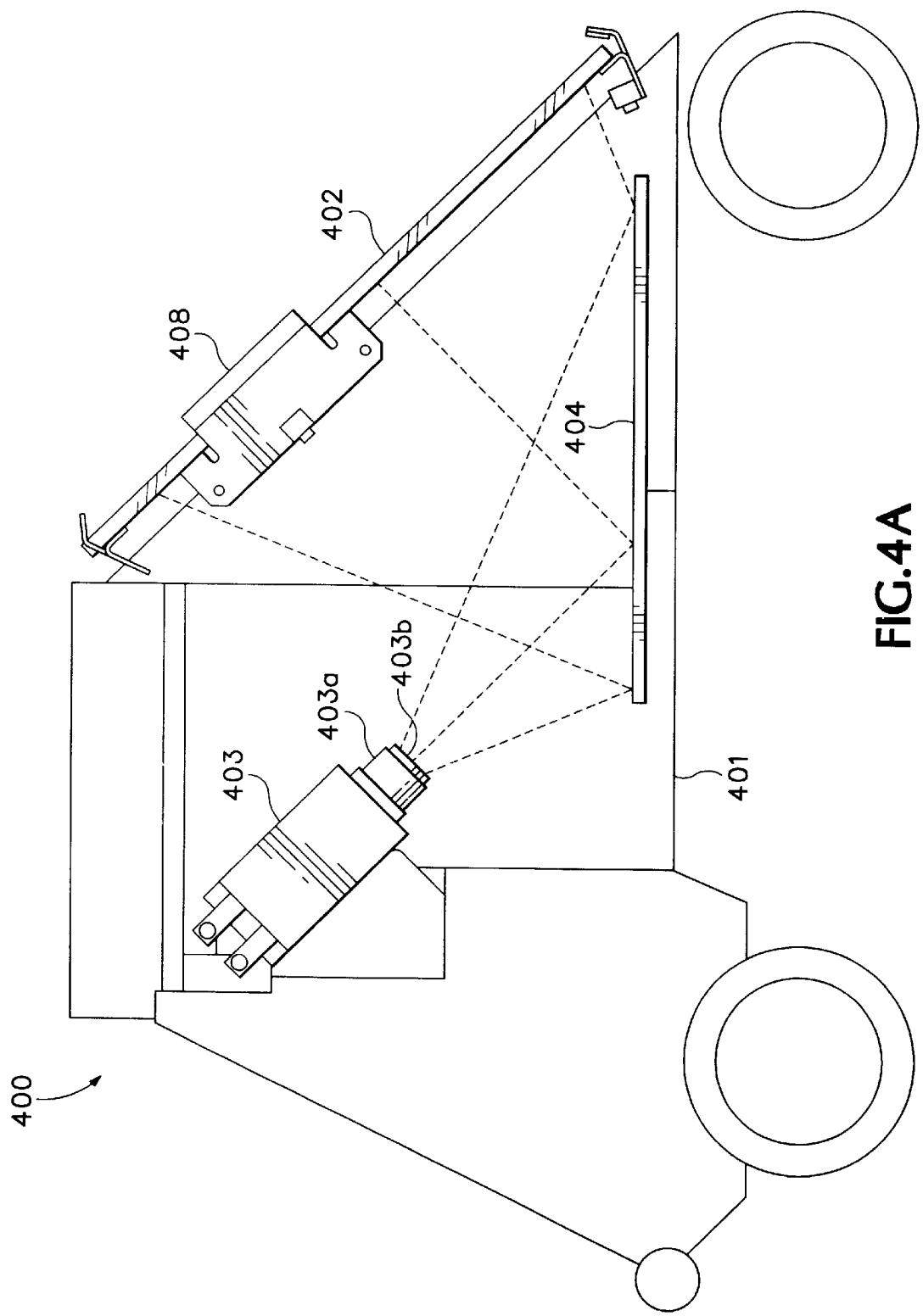
FIG. 4A shows a side view of one embodiment of a device which incorporates various aspects of the invention.

FIG. 4A shows in more detail one embodiment of the apparatus shown in FIG. 2. As shown in FIG. 4A, the device 400 includes a housing 401 which encloses a securely mounted camera 403 and a reflective mirror 404 positioned to reflect an image of the foot as received through transparent plate 402. Any type of electronic camera, such as a CCTV camera (to include MOS or CCD devices) may be used. Camera 403 preferably includes a primary lens 403a and a filter 403b. A plurality of optical illumination assemblies 408 (only one is shown in FIG. 4A) are arranged about the periphery of transparent plate 402 so as to illuminate the periphery of the foot. A computer controlled switch (not shown in FIG. 4A) allows the optical illuminators to be rapidly switched on and off by computer control. The primary lens 403a images the bottom of the foot, while a field lens (not shown in FIG. 4A) which is close proximity to the foot makes the lens system telecentric.

Figure 4B:
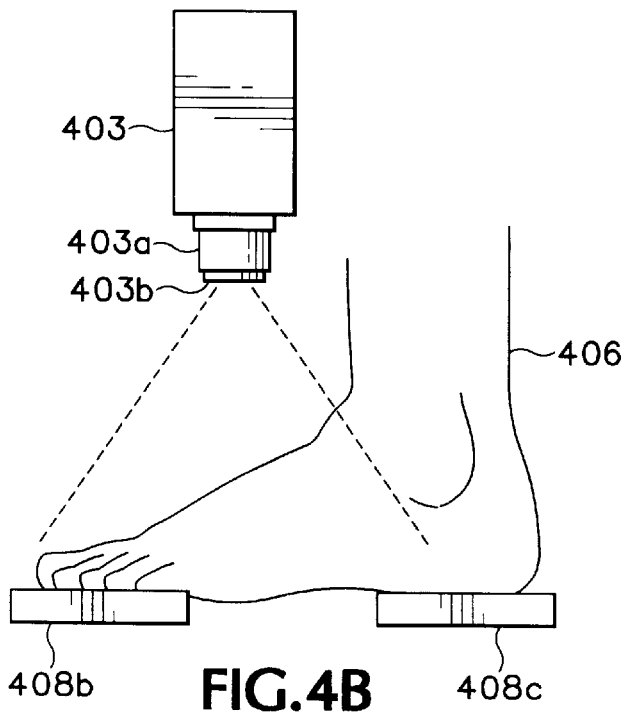
FIG. 4B shows a side view of an embodiment of a device which captures information without the use of a transparent plate.

FIG. 4B shows how various aspects of the invention may be practiced without the use of a transparent plate. In the configuration shown in FIG. 4B, camera 403 is disposed above foot 406, which is illuminated by near-infrared illuminators 408b and 408c (only two are shown). Camera 403 thus receives an image of foot 406 from above. To avoid occlusion of the image caused by the ankles, a second camera (not shown) may be added.

Figure 5:
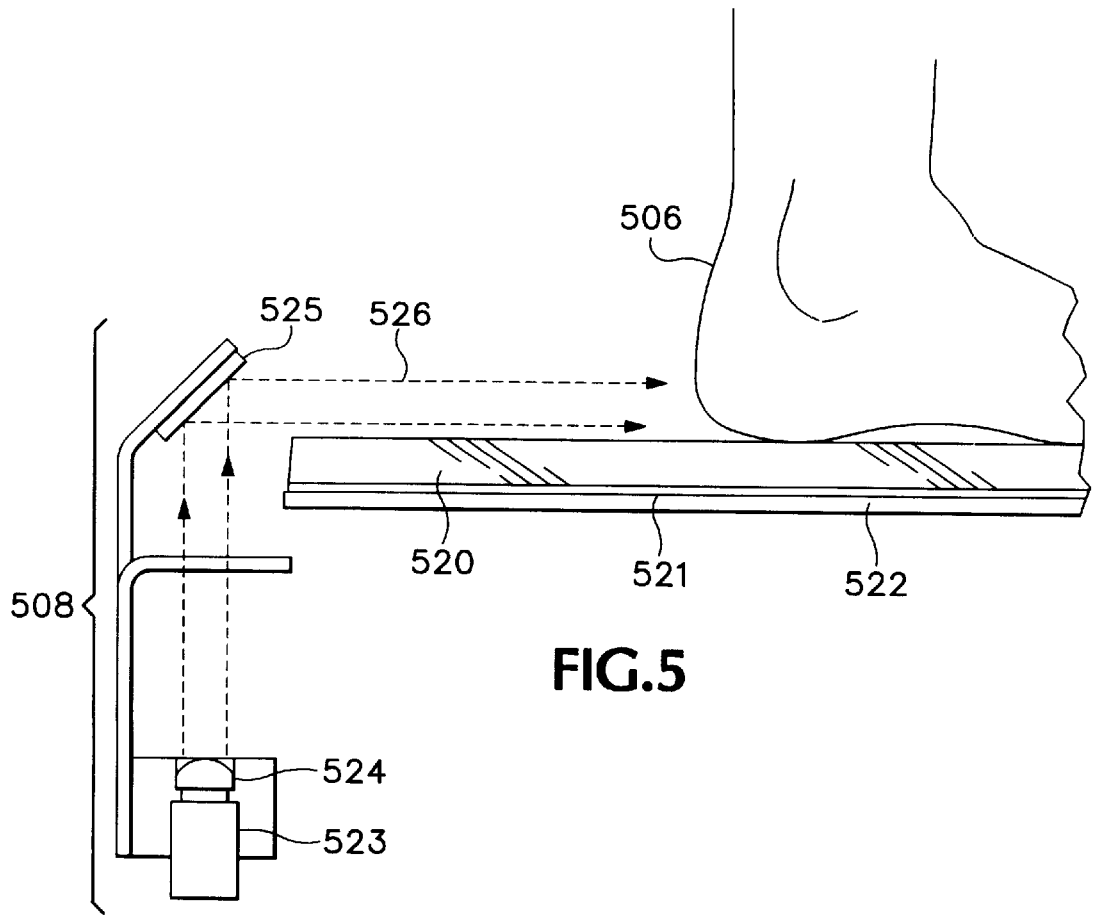
FIG. 5 shows a side view of a device according to various embodiments of the invention, including a rear optical assembly 508.

As shown in FIG. 5, for the embodiment of FIG. 4A a foot 506 is placed upon a transparent plate surface 520 such as clear plastic (acrylic or polycarbonate as examples) or glass. It is important that the plate be transparent to so-called "near infrared" light, but unimportant and even highly desirable that it be opaque to visible light. Hence, the term "transparent" as used herein refers to transparency of the desired wavelength range, not necessarily transparent to the human eye. Infrared transmitting glasses and plastics exist; however, they are relatively uncommon and expensive.

An inexpensive alternative is to use a pair of filters 521 which transmit complementary visible colors and to place them in contact with the transparent plate. For example, if one of the filters transmits only red and the other transmits only green, then placing the two of them together will result in a system which does not transmit visible light. Dyes which are designed to work in the visible range will typically be non-absorbing in the infrared range, and this has been shown to be true experimentally. Colored filters such as those from Rosco corporation (36 Bush Ave., Port Chester, N.Y. 10573) for use in theater lighting have been shown to work very well in this application. A Fresnel lens 522, discussed in more detail below, may be placed in close proximity to transparent plate 520 to improve the measurement accuracy.

Each optical illuminator 508 may be comprised of a plurality of components to achieve an optimum illumination effect. In particular, each optical illuminator may comprise a light emitting diode (LED) 523 which emits light in the "near infrared" range (i.e., at about 880 nanometers), a cylinder lens 524, and a mirror 525 positioned to reflect a "fan" of light onto the periphery of the foot. The "near infrared" range was specifically chosen for 3 reasons:

First, it was theorized and experimentally verified that yarns or thread from which socks are fabricated are dyed using dyes which are only effective in the visible region of the spectrum and that they would be inactive in the infrared. This allows the "natural" color of the material which would be translucent to prevail, thus making all fabrics appear to have the same reflectivity to a first order. This was verified experimentally for a wide variety of socks with the exception of 100 percent wool. Wool which contains even a small percentage of non-wool material such as elastic fiber is clearly visible in the near infrared. Negating the effectiveness of the pigmentation reduces potential dynamic range problems.

Second, in the event that a device using the inventive principles is used with bare feet, the effectiveness of melanin pigment which causes variations in the darkness of a person's skin is also minimized in the near infrared. This also helps alleviate potential dynamic range problems.

Third, potential background light problems from fluorescent lighting are minimized since fluorescent lights are designed to produce light which is predominantly in the visible region of the spectrum.

While an illuminated human extremity placed on transparent plate 520 will generally reflect light towards camera 403, much of the illumination light is instead scattered after penetration into the upper layers of human skin and/or clothing. Much of this scattered light will also be directed toward camera 403. Thus, the term "reflected" as used herein will be understood to also include such scattered light.

Generally speaking, LED structures can be grouped into two categories. The first group, comprising most LEDs, include a structure in which the emitter material is bonded to one electrode and a second electrode is attached to the center of the emitter material via a ball bond. If the output of such an LED is collimated using a lens, the result will be a beam with a relatively large angular divergence since the light from the entire LED chip can reach the lens. Furthermore, the LEDs are mounted in a depression which acts to reflect light which is emitted by the edge of the chip and thus increase the output power of the LED. The reflective structure also degrades the ability to collimate the beam. Finally, the ball bond in the middle of the chip often results in a dark spot in the emitted distribution should the lens system actually form an image of the emitter.

A second type of LED structure, and that which is preferred in various aspects of the present invention (Opto Diode part number OD148) has an emitter structure which aids in producing a well defined beam. The emitter is attached to a flat header as opposed to being placed in a cup which will reflect light emitted from the side of the emitter. More importantly, the second electrode is not a ball bond in the center of the emitter. Instead, the top of the emitter is covered by an electrode with a hole in the center through which light can escape. When collimated, this results in a beam with a smaller angular divergence and without the potential for a dark spot should the lens actually form an image.

As shown in FIG. 5, each illuminator assembly 508 preferably includes a cylinder lens 524 to collimate the LED beam in one dimension while allowing the second dimension to diverge, thereby forming a "fan" of light 526. Cylinder lens 524 can take on a number of form factors including piano convex and biconvex. The plano-convex form has lower optical aberrations which results in a beam which is more uniform and has lower divergence. The biconvex form, however, offers adequate performance for this system and is significantly less expensive since commonly available glass rod can be used, thus reducing the cost from a few dollars to a few cents per lens. A typical LED/cylinder lens pair produces a beam which is 0.5 inch high at the foot position and which spreads with a total fan angle of 90 degrees in the plane of the plate.

The fan of light 526 illuminates the peripheral side of the foot from the point at which it contacts the glass or plastic plate to the point at which the side of the foot is perpendicular to the plate. This is typically a distance of approximately 0.5 inches. It is highly desirable to prevent light from entering the side of the transparent window since such light could cause illumination of the underside of the foot.

The illumination control circuit (element 210 in FIG. 2) may comprise a set of electronic components which when commanded by a voltage level from either the serial or parallel bus of the control computer causes a transistor in series with the LEDs to change from a non-conductive to conductive state. A typical LED requires 50 mA and has a forward voltage drop of approximately 1.6 VDC. Placing 3 LEDs in series allows them to be powered directly from the +5VDC bus which is the bus with the greatest current capacity in normal PC's.

Referring again to FIG. 4A, the viewing system may be comprised of a camera 403, a primary lens 403*a*, a band pass filter 403*b*, an optional neutral density filter (not shown) and a field lens (element 522 in FIG. 5). The camera should be chosen to have high sensitivity in the near infrared range. CCD chips are fabricated from silicon which nominally has high sensitivity in the 800–950 nanometer wavelength region; however, since most CCTV cameras are used in the visible spectral region, the response of most CCTV cameras is modified with a filter to block the near infrared and transmit only the visible. Only a few cameras either lack a filter or have a filter which can be removed and hence have the appropriate spectral response. An example is the model CV-235E from Motion Analysis (Eugene, Ore.). It is preferable to operate the camera with the AGC off. If the AGC is left on, the camera may change gain in between the LED on/LED off exposures and imperfect background substraction may result. It is also important to operate the camera such that it is not saturated.

The primary lens 403*a* is preferably attached to the camera and produces an image of the active region on the transparent plate in a nominal area of 15×4 inches. A short focal length lens such as 4 mm when combined with a 0.5 inch format CCTV camera produces a compact system having a lens to transparent plate distance of only 12 inches.

A band pass spectral filter 403b may be installed on lens 403a to improve the contrast of the optical system and to discriminate against background light sources. If each LED in the illuminators has a center wavelength of 880 nanometers and a bandwidth of 50 nanometers, this should ideally be matched by spectral filter 403b. It is possible to also use a simple infrared pass filter such as Schott RG850 which passes infrared while blocking light with wavelengths shorter than 850 nanometers. This is a less expensive solution; however, it passes more ambient light than does a true band pass filter.

It is desirable to operate the LEDs at as high a power level as possible and to stop the camera lens 403a down to avoid saturation. If the camera lens is stopped down excessively, however, the system resolution will be affected since diffraction effects will come into play. For standard resolution 0.5 inch format CCDs and 880 nanometer light as an example, stopping the lens to F/10 reduces the modulation transfer function to approximately 0.5. It is therefore desirable to use as low as F stop as possible for resolution reasons. If it is necessary to stop the lens to F/8 or higher, then it is advisable to use a neutral density filter to reduce the light level instead of the aperture stop on the lens.

One problem which is exacerbated by the use of a short focal length primary lens is that the rays at the edge of the object field come from the object at a significant angle which makes it impossible to see the true length of the toes and heel for example. This problem can be remedied in large part by placing a lens having a focal length equal to the object to primary lens distance, as close to the object plane as possible. If the field lens is virtually in the object plane, it will have little effect upon the focus of the primary lens nor upon the system magnification. The only first order effect will be to make the optical system telecentric, which is to say that the rays at the foot will be perpendicular to the transparent plate upon which the foot rests. It is preferable that the lens be aspherized to correct for third order spherical aberration since the numerical aperture of the field lens is very high. If it is not corrected, the rays at the edge of the field and those at the center of the field will not focus at the same point and vignetting over part of the field will occur.

Aspheric lenses having F numbers of 1 are generally impractical if fabricated from glass. The only practical manufacturing method for creating large, high speed aspheric lenses is by compression or injection molding the lens in the form of an aspheric Fresnel lens. Fresnel Optics (Rochester, N.Y.) makes an aspheric Fresnel lens (part number SC240) which has a focal length of 317 mm which is suitable for use as a field lens. Field lens 522 is shown in FIG. 5 positioned beneath transparent plate 520.

Referring again to FIG. 2, frame grabber 207 "grabs" a frame of video from the camera and digitizes it. The digitized image can then be read into the memory of computer 205 where the image may be manipulated to produce as an example an image with the background subtracted. Computer 205 may comprise any general purpose digital computer such as a common "PC" class machine.

Computer program 211 causes illumination control circuit 210 to switch to turn the LEDs on and off and frame grabber 207 to grab and digitize a frame of video, and to store the digitized video in the computer memory. It also processes the video to produce information relating to the size and shape of the foot and outputs the information to an output device as explained in more detail herein.

Input device 213 enables an operator to communicate with computer 205. It may be as elaborate as a full keyboard such as found on a PC or as simple as a switch which toggles the computer from operation to operation. For example, a push button switch may be used to cause computer 205 to grab a frame of data and process it.

A description of computer program 211 (FIG. 2) will now be provided with reference to additional figures. In general, the following description explains how images are captured and processed to generate size and shape information from extremities placed on transparent plate 202.

Figure 6:
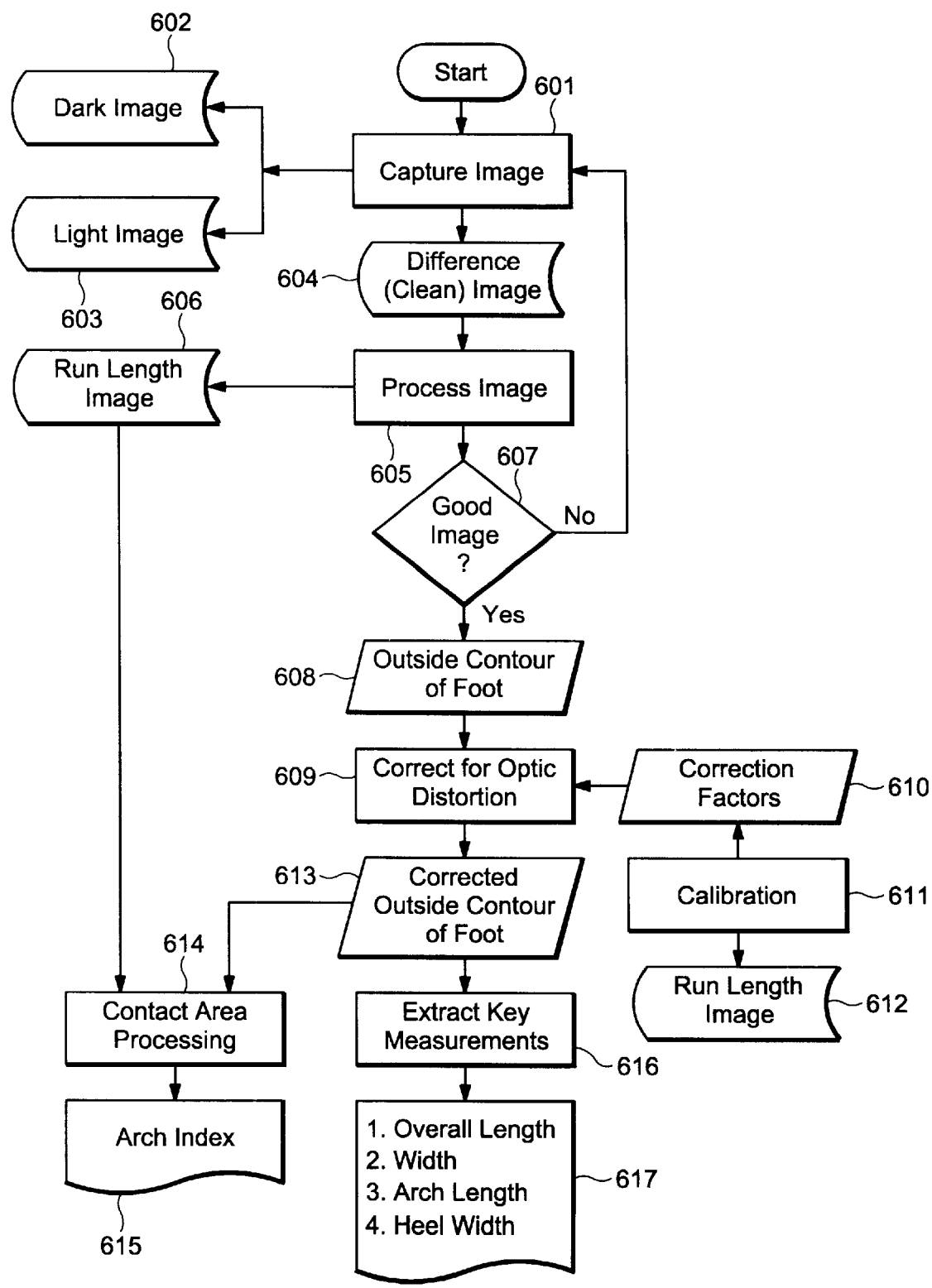
FIG. 6 shows an overview of the sizing process which obtains detailed measurements.

FIG. 6 shows an overview of the sizing process which obtains detailed measurements. This process may be implemented in computer program 211 in computer 205. While the process will be described with reference to a foot, it will be appreciated that this is by way of example only and other extremities or objects may be used.

As shown in FIG. 6, the process generally includes a first step 601 of capturing two images of the foot including a "dark" image 602 (i.e., non-illuminated foot) and a "light" image 603 (i.e., an illuminated foot), then subtracting them to produce a difference image 604.

In step 605, the difference image is processed, creating a run length image 606. If the image is determined to be a good image (step 607), then processing continues in step 608 which determines the outside contour of the foot. In step 609, a correction for optic distortion is performed based on correction factors 610 which are assumed to have been created using a calibration process 611.

In step 613, a corrected outside contour of the foot is provided to a contact area processing step 614 which results in an arch index 615, and to a key measurement extraction step 616 which results in additional measurements.

In general, image processing (step 605) includes steps of converting the gray scale image from the frame grabber into a pure black and white image; encoding the image into a "run length" format 606; locating all of the objects in the image; selecting the foot and removing the other objects from the image; generating an outside contour of the foot; and collecting an initial estimate of key measurements. The result is an outside contour of the foot 608 in the coordinate system of the original image.

The purpose of correcting for optic distortion (step 609) can be generally summarized as follows. The contour coordinates of the original image cannot be simply multiplied by a correction factor. Because of the wide angle of view, the image must have an optical correction applied to it. Using this optic correction allows the physical device to be more compact.

Contact area processing (step 614) can be generally summarized as follows. The contact area of the foot shows up as a dark area inside the foot image. By analyzing the dark image, the arch index can be produced. The arch index is correlated to arch height. Processing the contact area to produce arch index generally includes the following steps: (1) creating a run length image of the dark area; (2) checking to see that all parts of the dark image belong in the image; (3) breaking up the run length to improve area estimates; (4) calculating the approximate areas of each run length; and (5) dividing the run lengths in the three separate areas.

Key size extraction (step 616) can be generally summarized as follows. With the contour coordinates translated into actual size, the contour is rotated so that size measurements can be extracted. Steps which can be used to align the contour include: (1) fitting a circle to the heel of the foot; (2) rotating around the heel center using the first metatarsal head; and (3) using the correctly aligned data to determine length, width, and arch length.

Calibration (step 611) is generally performed before operation is begun and the results are applied during the optic correction step (step 609). The process of calibration generally involves the following steps: (1) capturing an image of a special calibration target; (2) determining the optic center; (3) determining the focal length; and (4) setting the overall conversion factor.

Since one aspect of the invention contemplates use in a retail environment, one goal is to provide data in real time. The software processing and hardware should be optimized to operate in normal store lighting, ideally capturing the dark and light images in less than 100 ms and the total processing time should be less 1 second. With the approach described herein, this goal can be achieved with currently available personal computer technology.

Figure 7A:
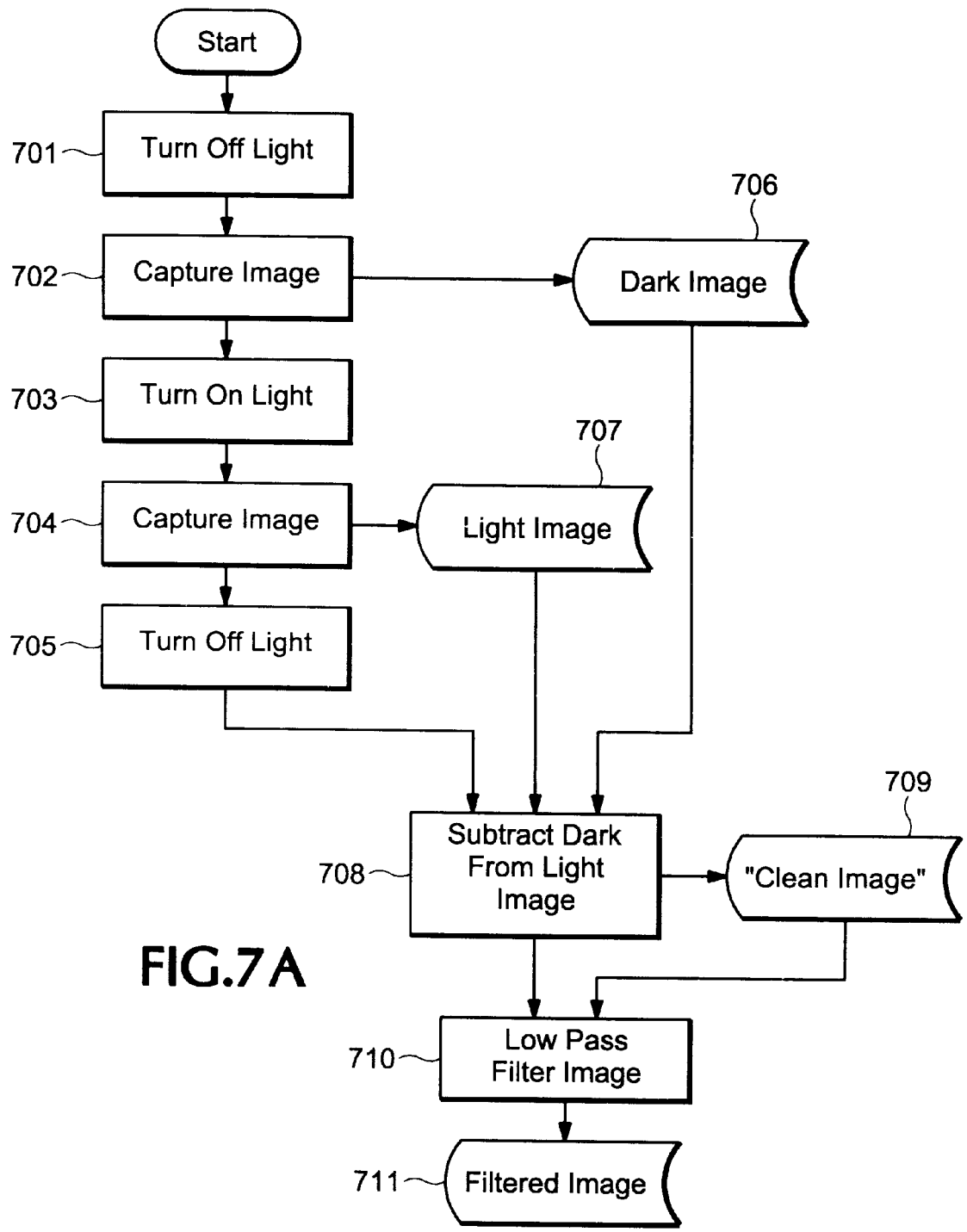
FIG. 7A shows additional detail of one possible implementation of step 601 of FIG. 6.

FIG. 7A shows additional detail of one possible implementation of the image capture step 601 which generally controls the video digitizing hardware and illumination of the foot. The process begins with step 701 in which the optic illumination assemblies are turned off. In step 702, an image of the non-illuminated foot is captured by way of frame grabber 207 (FIG. 2), producing a "dark" image 706 of the foot. Next, in step 703, the optic illumination assemblies are turned on, and the resulting image is captured in step 704, producing a "light" image 707 of the foot. In step 705, the illumination is again turned off.

The hardware used for image capture may include two distinct subsystems: a computer controlled illumination system (see optical control element 210 and illumination assemblies 208a and 208d in FIG. 2) and the image acquisition circuitry (see camera 203 and frame grabber 207 in FIG. 2) which are both controlled by computer program 211 operating in computer 205.

In step 708, the dark image 706 is subtracted from the light image 707, resulting in "clean" image 709. It should be recognized that the opposite subtraction could instead be performed with equivalent results. By subtracting the two images, the ambient light is removed from the clean image. This allows the device to be used in a retail environment provided there is not light directly pointing at the device.

Next, clean image 709 is passed through a low pass filter process 710, creating a filtered image 711. Low pass filtering is used to reduce the noise in the image. The result is an average contour that is less sensitive to local noise.

Figure 7B:
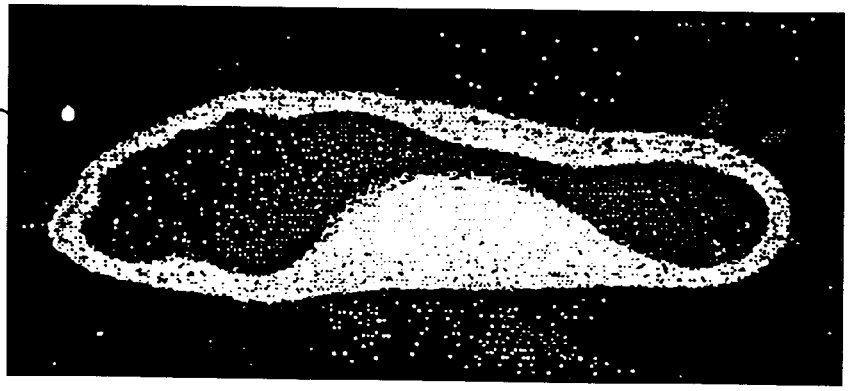
FIG. 7B shows graphically the effects of generating a dark image 706, a light image 707, and a difference image 709.
Figure 7B:
Figure 7B:

FIG. 7B shows graphically the effects of generating a dark image 706, a light image 707, and a difference image 709. The purpose of subtracting the light and dark images is to remove light attributable to the external environment. To be effective, the foot should not move between the light and dark image capture steps. In the dark image case, the foot acts as a mask, blocking out any environmental light in its path. During light image capture, the foot is illuminated on its side with infrared light. This produces a large difference underneath the foot. Any environmental light will be present in both the light and dark images, ideally producing the same levels. The light spot in the lower right of FIG. 7B is an example of an environmental light that is subtracted away in the final image.

The subtraction operation requires some care to preserve the coding of the image. The image may be stored as a gray scale with one unsigned byte (8 bits) representing each pixel. There is the potential for the subtraction of the dark image from the light image to produce a negative result. All negative values are set to zero.

Figure 7C:
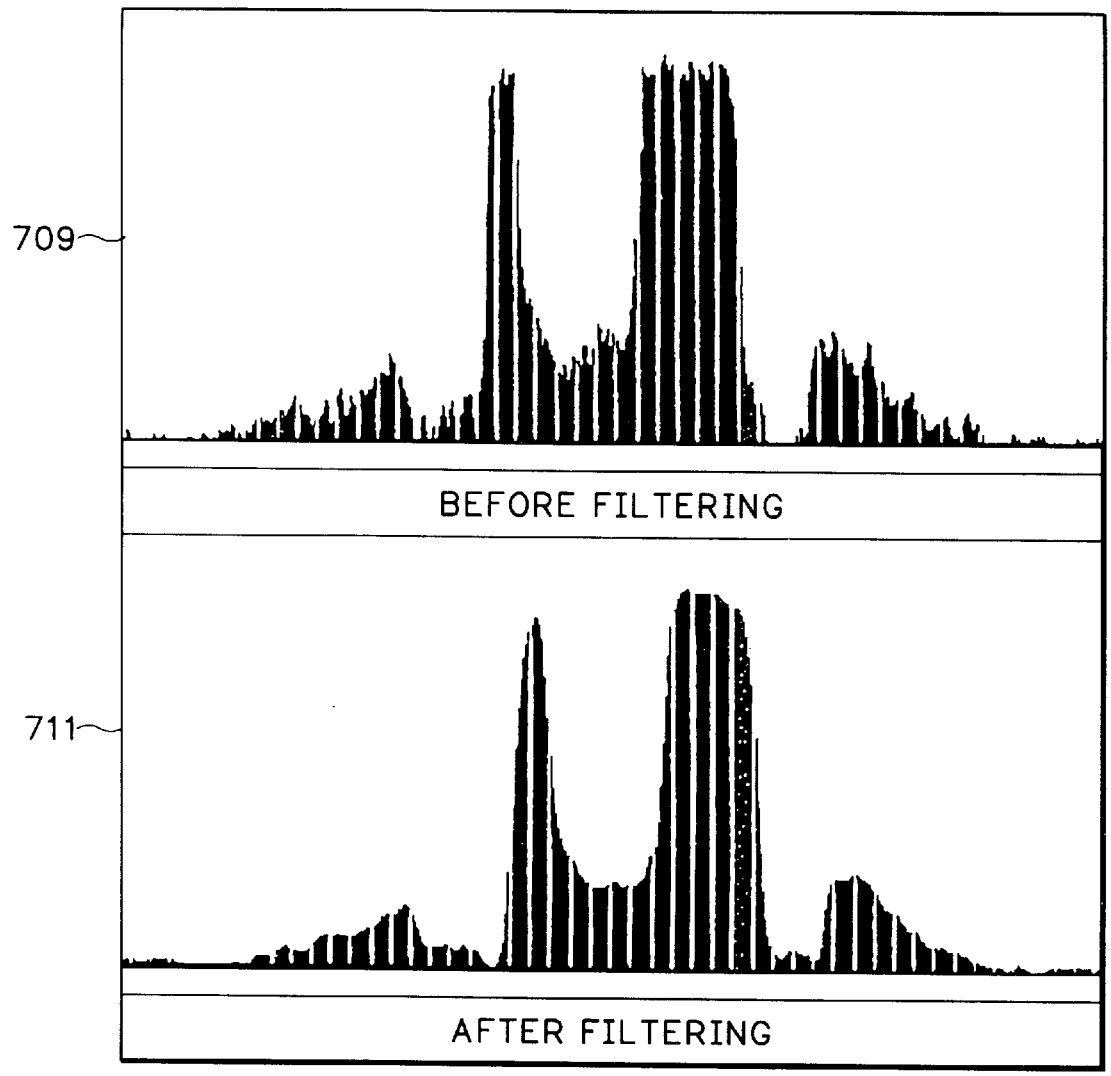
FIG. 7C shows graphically the effects of low pass filtering the difference image 709 to produce a filtered image 711.

FIG. 7C shows graphically the effects of low pass filtering the difference image 709 to produce a filtered image 711. The difference image generally contains low level noise due both to the camera and the frame grabber hardware. The effect of this noise is to produce small scale irregularities in the foot outline. This could potentially affect measurements if they occur at critical locations. Since the noise appears as spikes on the normal video signal (see FIG. 7C), it has a higher frequency than the video signal. The noise can thus be removed using a low pass filter. The low-pass filter may be implemented as a simple recursive algorithm applied in both the forward and backward directions to both row and columns of the image. By applying the algorithm in all four directions, the symmetry of the image is preserved.

Figure 8A:
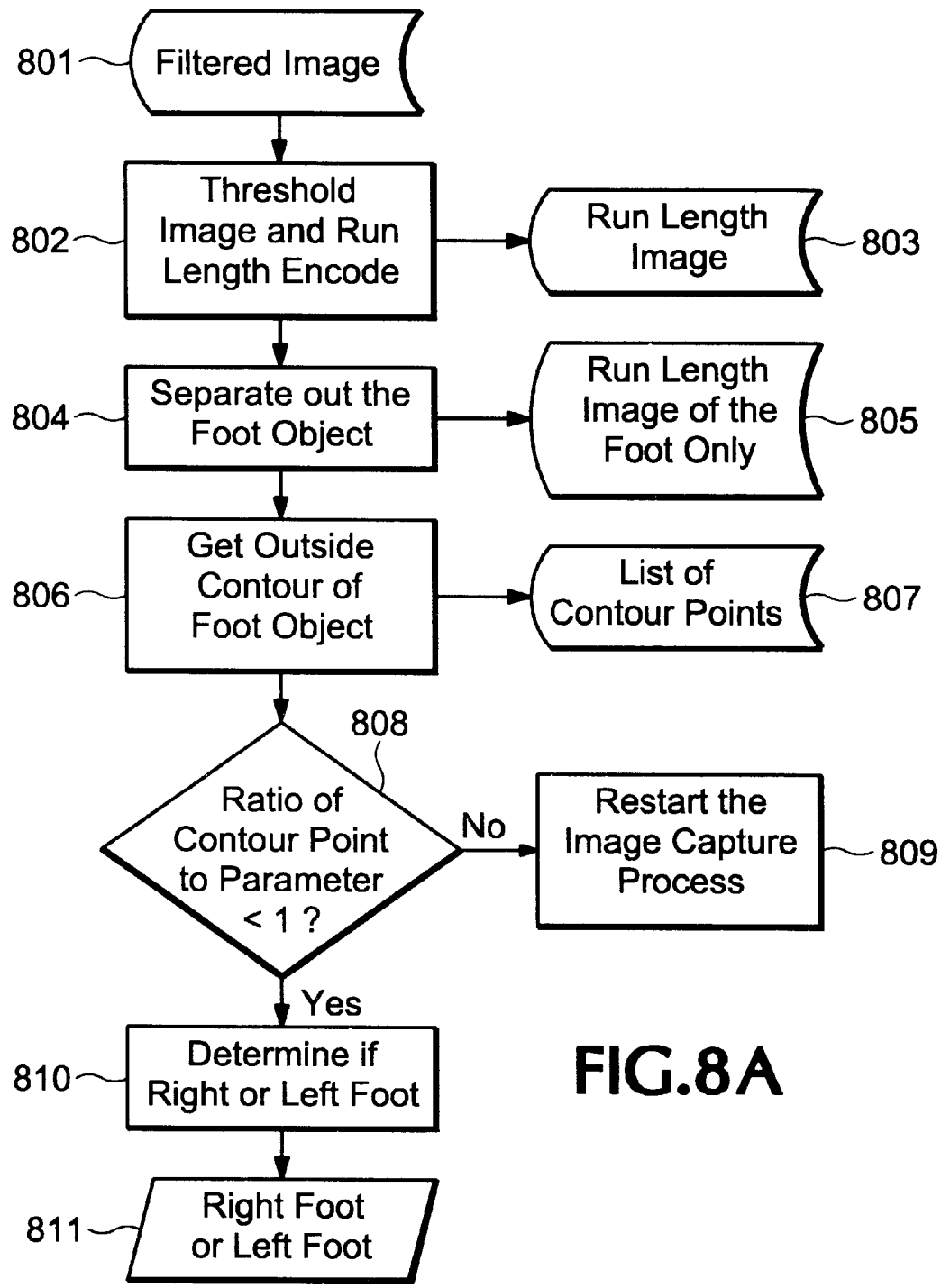
FIG. 8A shows additional details for one possible implementation of the image processing step 605 of FIG. 6.

FIG. 8A shows additional details for one possible implementation of the image processing step (element 605 of FIG. 6). In general, the image processing step (element 605) is shown in successively greater detail in FIGS. 8A, through 8G.

One objective of the image processing step is to identify the foot in the image and produce an outside contour of the foot from which measurements are produced after correction for optical distortions. Also, a determination is made as to whether the image represents a left foot or right foot, which can be used to identify key features during later states of processing.

Figure 8B:
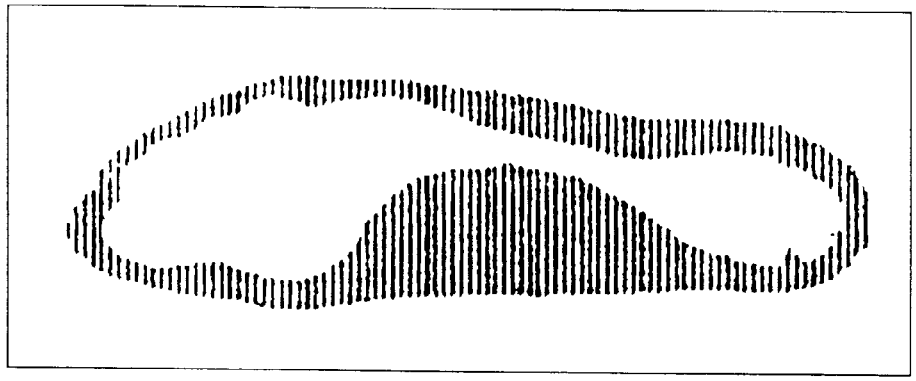
FIG. 8B shows a graphical representation of the thresholding and run length encoding of FIG. 8A.
Figure 8B:
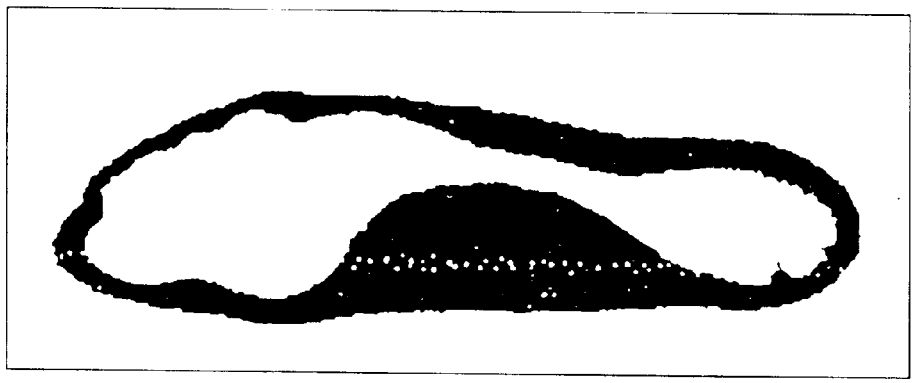
Figure 8B:
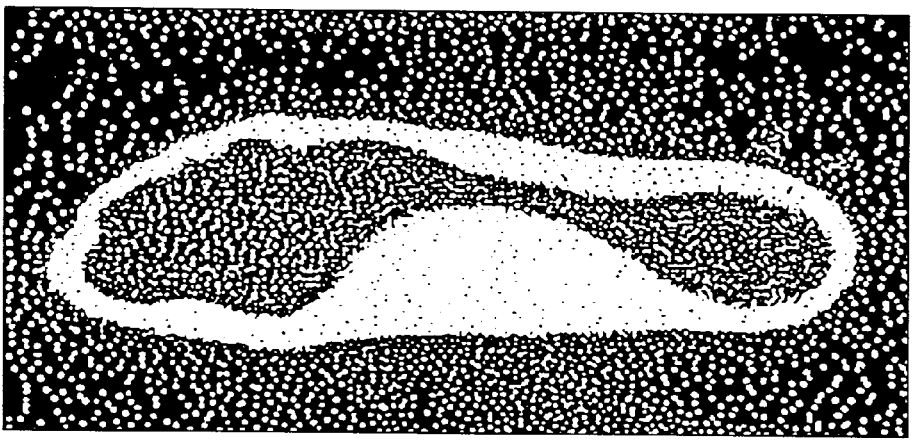

Beginning in step 802, the filtered image 801 may be coded in 8 bit gray scale with 255 as pure white and 0 as pure black (other mapping schemes are of course possible). Using this scheme, the foot will appear as a white image on a black background. Step 802 converts each gray scale pixel into either a black pixel or white pixel depending on whether the gray scale value exceeds a predetermined threshold value. At the same time, the image may be compressed using run length coding. A pictorial representation of this process is shown in FIG. 8B.

A threshold value can be selected based on empirical experiments for a particular set of hardware; no specific value is critical for all applications. Values above the threshold value are set to a pure white value; those below the threshold are set to a black value.

At the same time pixels are separated into black and white, the result can be compressed using a run length code. The run length code is done on a row by row basis. For this application, a slight variation on the conventional run length coding scheme can be used. In particular, only white lines are recorded. Also, the start and finish column values are recorded. An array of run length points can thus take the following form:

| Row | Start Column | End Column | Flags |
|-----|--------------|------------|-------|
| 130 | 90           | 300        | 0     |
| 131 | 85           | 100        | 0     |
| 131 | 270          | 310        | 0     |
| 132 | 82           | 95         | 0     |

The run length array can be sorted in increasing row order then column order. This allows algorithms applied to this data to make assumptions that speed up processing.

In step 804, the foot object is isolated from the image. Most of the remaining non-foot objects are artifacts of the illumination system. They are normally significantly smaller than the foot object. The process used to isolate the foot can be implemented in two parts: (1) separate all of the individual run length lines into unique connected objects; and (2) copy out the largest object (the foot object). One approach is to start with the first line in the run length array and separate the image into connected object. The connection in this case means at least one pixel directly under pixel in the run length above.

Figure 8C:
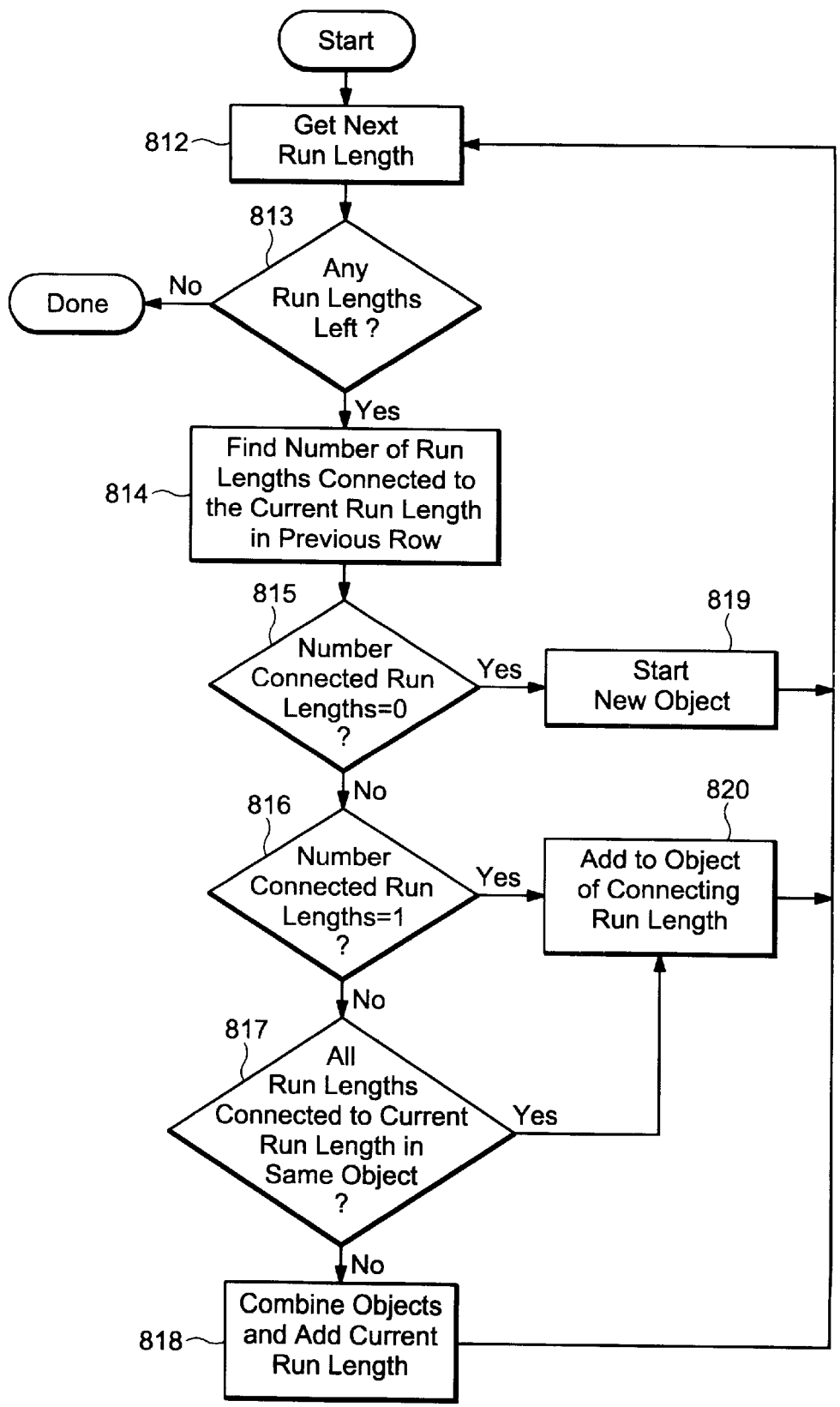
FIG. 8C shows various steps which may be used to isolate a foot object from an image (step 804 of FIG. 8A).

One possible approach for isolating the foot object from the image (step 804) is shown in FIG. 8C. Beginning in step 812, the next run length from the image is examined. In step 813, a test is performed to determine if any run lengths remain and, if not, the process terminates. Otherwise, in step 814 a search is conducted to find any run lengths from the previous row that are connected to the current run length. The number and identity of any connected run lengths is determined.

A test is performed in step 815 on the number of connected run lengths found in the previous step. If none were found, then in step 819 the current run length becomes the first member of a new object. If a connecting run length was found, then in step 816 a test is made to determine the number of connections is equal to one, in which case (step 820) the current run length is made part of the same object as the connected run length.

If there is more than one connected run length (i.e., the only remaining possibility), then in step 817 a check is made to determine which object each connected run length is a part of. If they are part of the same object, then step 820 is executed, and the current run length is added to that object. Finally, if the current run length is connected to run lengths listed in different objects, this indicates that the current run length represents a connection between the two objects, and in step 818 the two connected objects are combined, and the current run length is added to it. Thereafter, processing resumes at step 812.

Figure 8D:
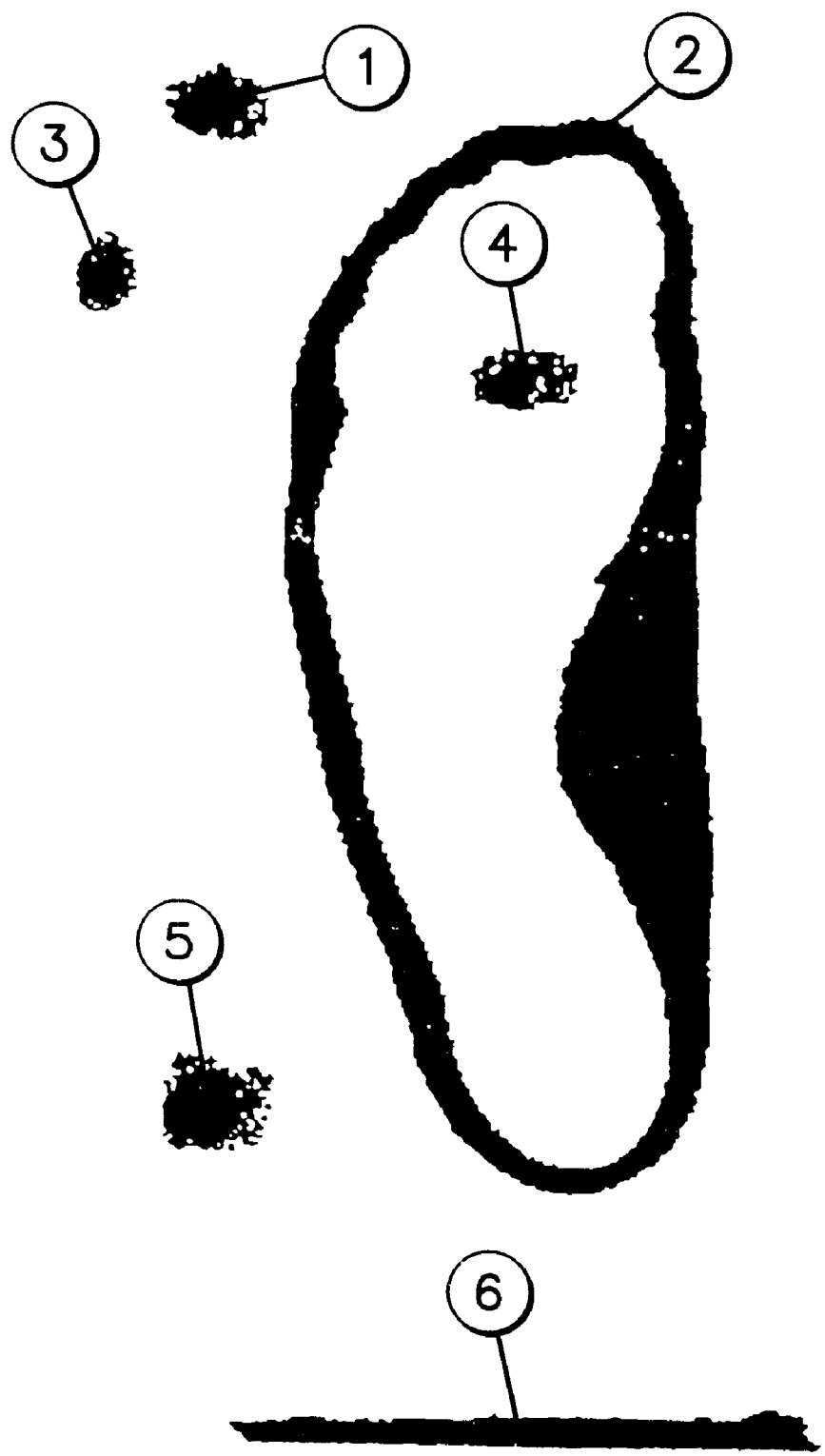
FIG. 8D shows the result of the process shown in FIG. 8C.

The result of the process depicted in FIG. 8C is a set of numbered objects as shown in FIG. 8D. Once the image has been divided into connected objects, the foot object is assumed to be the largest object. Once the foot is identified, the other objects are removed and all further processing is done on the foot run length data only.

Figure 8E:
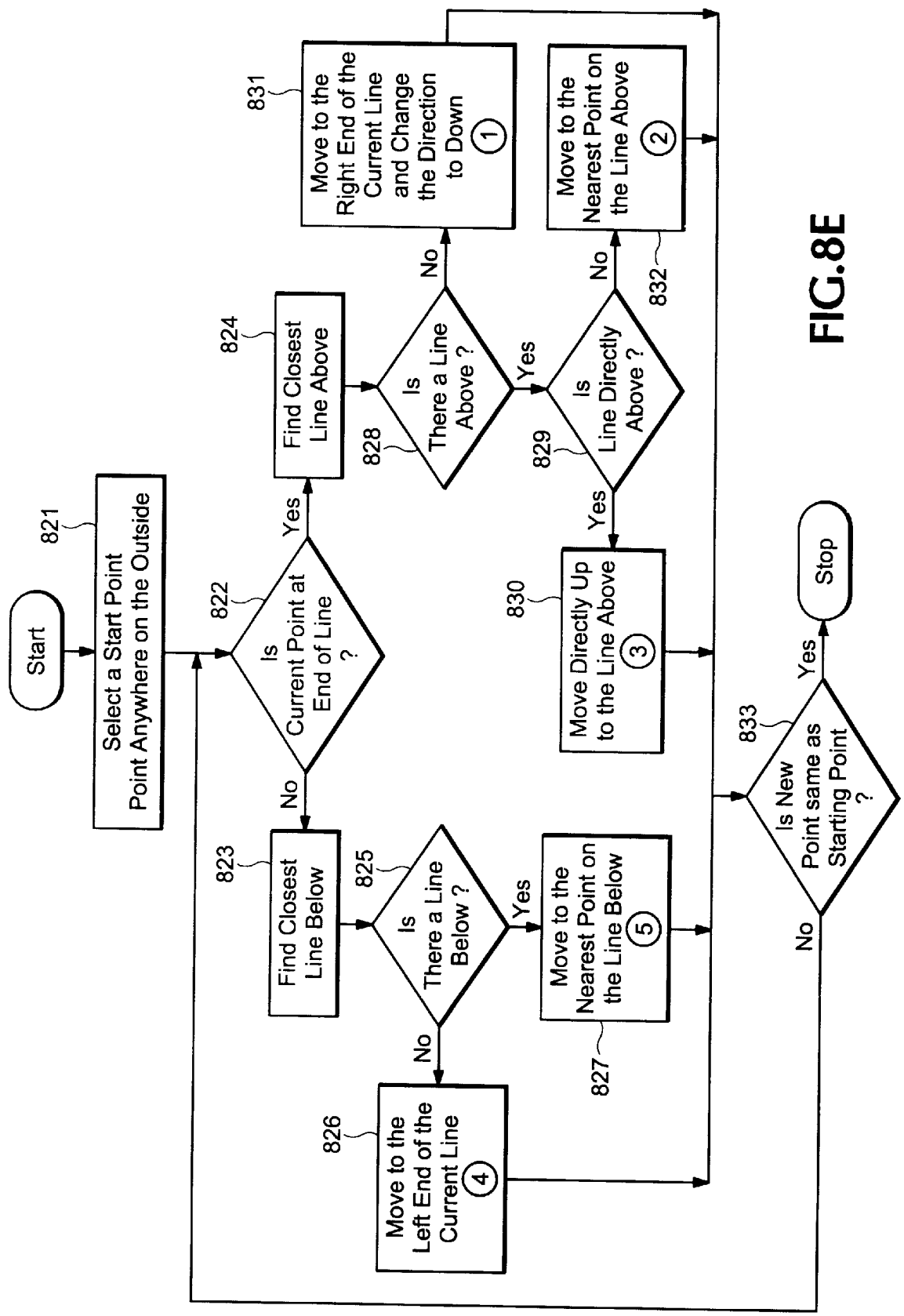
FIG. 8E shows various steps which may be used to implement step 806 of FIG. 8A.
Figure 8G:
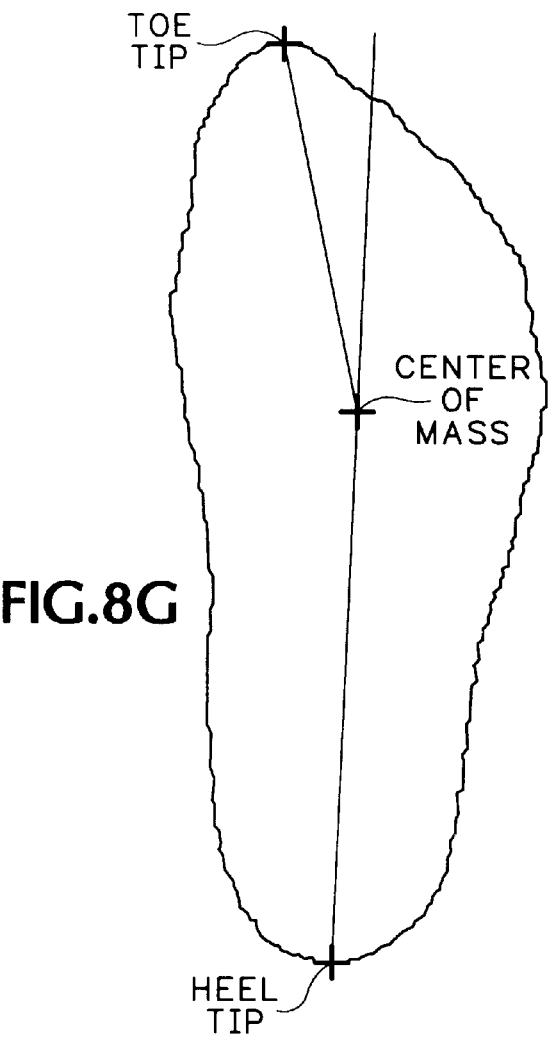
FIG. 8G shows a process for determining whether an image represents a left foot or a right foot (step 810 of FIG. 8A).

Referring again to FIG. 8A, the next step of image processing is to determine the outside contour of the foot (step 806). One process for performing this step is depicted in FIG. 8E and illustrated graphically in FIG. 8F. Most of the measurements needed to carry out various inventive principles are made on the basis of the foot outline only. The outline can be obtained from the run length foot data by taking the contour. Generally speaking, a point on the outside of the foot object is selected and the steps shown in FIG. 8E can be used to "walk" point by point around the outside of the contour. In FIG. 8F, the run lengths are shown as rectangles. The numbers in circles next to paths match the numbers in circles shown in FIG. 8E.

Beginning in step 821 of FIG. 8E, the next contour point in the image is located. In step 822, a test is made to determine if the current point is at the end of a line. If so, then step 824 is executed; otherwise, processing advances to step 823. In step 823, the closest line below is located. Next, in step 825, a test is performed to determine whether a line below exists. If not, processing advances to step 826; otherwise, step 827 is executed. After step 827, a test is made in step 833 to determine whether the new point is the same as the starting point and, if so, processing terminates.

In step 824, the closest line above is located. In step 828, a test is performed to determine whether a line above exists and, if not, step 831 is executed (the right end of the current line is moved and the direction is changed to "down"). Otherwise, step 829 is performed, in which a test is performed to determine whether a line directly above exists. If not, step 832 is executed, and movement is made to the nearest point on the line above. Otherwise, step 830 is executed, and movement is made directly to the line above. After step 830, a test is made in step 833 to determine whether the new point is the same as the starting point and, if so, processing terminates.

The result of contour following is a set of points in X and Y that move clockwise around the outside of the foot.

Once the contouring procedure is complete, the image process is checked for potential problems in the original image capture. Referring back to FIG. 8A, in step 808 the ratio of contour points to peripheral points has been found to be a sensitive indicator of problems and, accordingly, a test is performed to determine whether this ratio is less than 1. The number of contour points is obtained from the size of the data structure. The number of peripheral points is obtained by getting the minimum and maximum height and width values and constructing a rectangle around the foot object. The number of points in the rectangle periphery is the value used. A ratio above one indicates a problem. The typical problem found are pants cuffs or improper illumination. If the ratio is not less than 1, then in step 809 the image capture process is again restarted.

Referring again to FIG. 8A, in step 810 it is determined whether the data as processed represents a left foot or right foot. This can be done using a four step process, illustrated graphically in FIG. 8G: (1) find the center of mass of the foot using the outside contour; (2) find the farthest point above the center of mass (Toe Tip); (3) find the farthest point below the center of mass (Heel Tip); and (4) draw a line through the heel tip and the center of mass. If toe tip is to the left, it is a right foot.

Referring again to FIG. 6, the next step (step 609) is to correct for optical distortion in the image. Because of the short focal length required to keep the device compact, the points must be correct to produce the final measurements. The pixels in the image obtained from the camera represent the angle of the light rather than the actual location. The optical correction changes these angles into actual distances.

Figure 9:
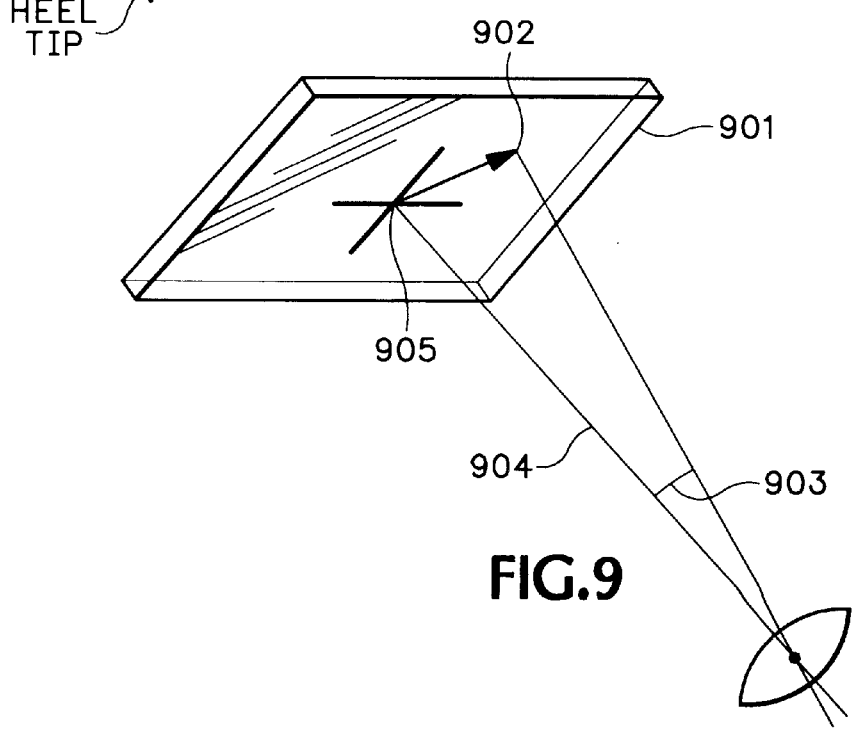
FIG. 9 shows optics correction geometry for making optics corrections.

Since each pixel represents an angle, the conversion can be performed using simple trigonometry. The actual location of a point in the image can be obtained by the following steps: (1) determine the number of pixels from optic center to point of interest; (2) multiply by a conversion factor from pixels to angle; (3) find the actual distance using : (Focal Length)* tan(Photo Angle); and (4) based on the proportions in the original photo, generate actual X and Y locations of the point. FIG. 9 shows the optic corrections geometry. The transparent plate is indicated by element 901; an actual point is represented by element 902; the photo angle is indicated by element 903; the focal length is shown by element 904; and the optical center is indicated by element 905. As this conversion process is well known, no further elaboration is necessary.

Figures 10A, 10B:
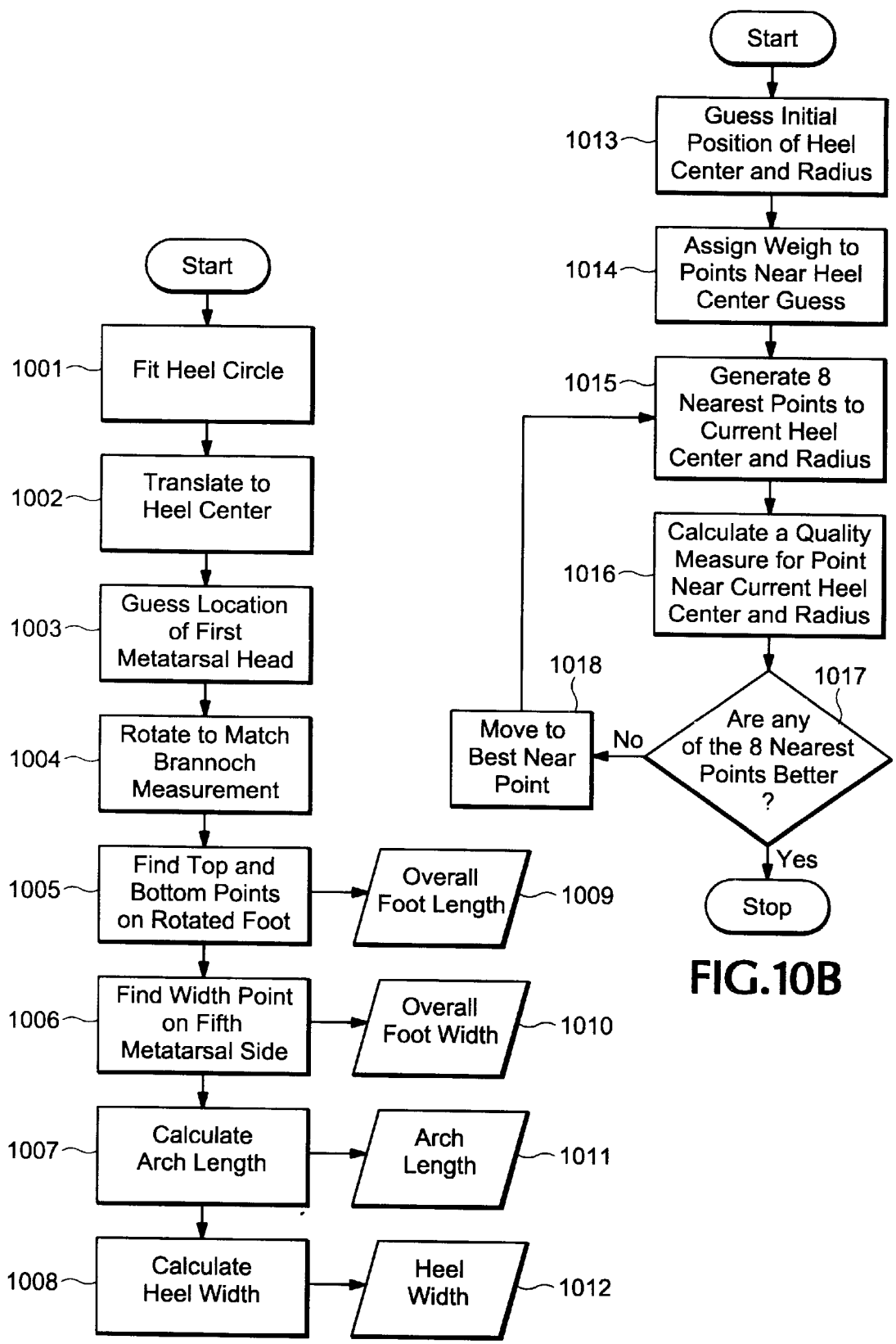
FIG. 10A shows steps of a process for extracting key measurements from corrected contour information.
FIG. 10B shows additional detail of step 1001 of FIG. 10A.

Referring again to FIG. 6, the next step (step 616) involves extracting key measurements from the corrected contour information. In other words, the contour information is converted into foot dimensions. The image of the foot is also aligned so that standard measurements can be extracted. FIG. 10A shows one process which can be used to obtain this alignment. The steps shown in FIG. 10A will be explained in more detail with reference to FIGS. 10B, 10C, 10D, and 10E.

In FIG. 10A, at step 1001 (the first step in the alignment process) a circle is fit to the heel. This can be done using the process illustrated in FIG. 10B, to which reference will now be made.

Figure 10C:
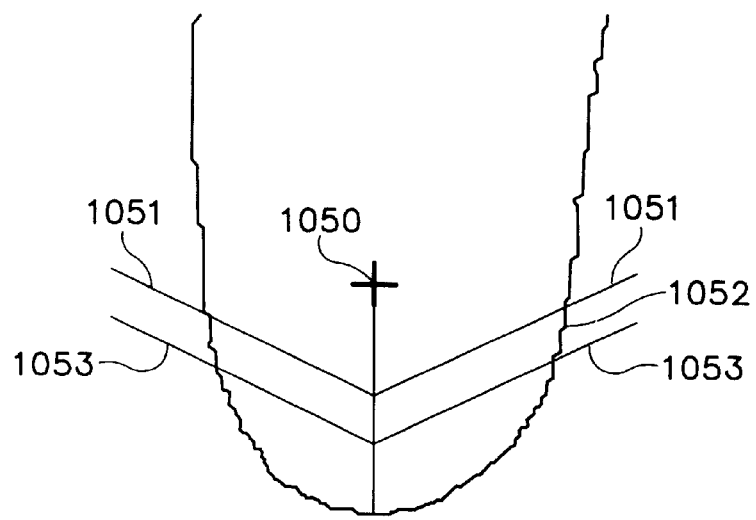
FIG. 10C illustrates graphically a procedure for estimating the initial position of a heel center and radius.

Referring to FIG. 10B, beginning in step 1013, the initial position of the heel center and radius is estimated. An important factor in determining the fit of the heel circle is the weighting factor used. One possible weighting factor, chosen based on empirical analysis, is described below. The function is designed to include mainly points below radius point. Lines with 2:1 slope were used to provide some protection from foot skew. FIG. 10C illustrates graphically this procedure, in which reference numeral 1050 represents an initial guess at the heel center; reference numeral 1051 indicates a line above which no points are used; reference numeral 1052 indicates an area in which points are weighted from 1.0 to 0.0; and reference numeral 1053 indicates a line below which points are given a weight of 1.0.

Weights can be varied linearly from line 1053 to line 1051. A point that falls on or below line 1051 can be given a weighting value of 1.0, while a point that falls on or above line 1051 can be given a weighting value of 0 (i.e., it is not considered). A point midway between line 1053 and line 1051 can be given a weighting value of 0.5. The following equations can be used to determine a "quality measure":

distance error=(distance from current point to trail heel center)
MINUS (trial radius)

point error=(weighting factor)*(distance error)

quality measure=sum of absolute values of all point errors

Although the configuration of region 1052 can be varied, one possible set of dimensions is as follows. Assuming a heel radius of 1.3 inches, the two 1053 lines can be positioned along the radius at distances of 30% of the heel radius, and the two 1051 lines can be positioned at 50% of the heel radius.

Referring again to FIG. 10A, in step 1002, once the center of the heel is located, it is used as a point of rotation (i.e., translated to the origin of the cordite system).

Thereafter, in step 1003, an estimate on the location of the first metatarsal head is made based on the traditional Brannoch arch length measurement (⅔ of foot length plus ½ inch for adults). An initial alignment is done using a line passing through the heel circle center and 1.5 inches from the initial guess at the first metatarsal head. See FIG. 10D, in which reference numeral 1054 represents an initial guess at the first metatarsal head; reference number 1055 represents a 1.5 inch length, and reference number 1056 represents a heel circle center. Final alignment can be done by looking for a point near the guessed value of the first metatarsal head further from the current center line. The furthest point is used and a final rotation calculated and applied.

Figures 10D, 10E:
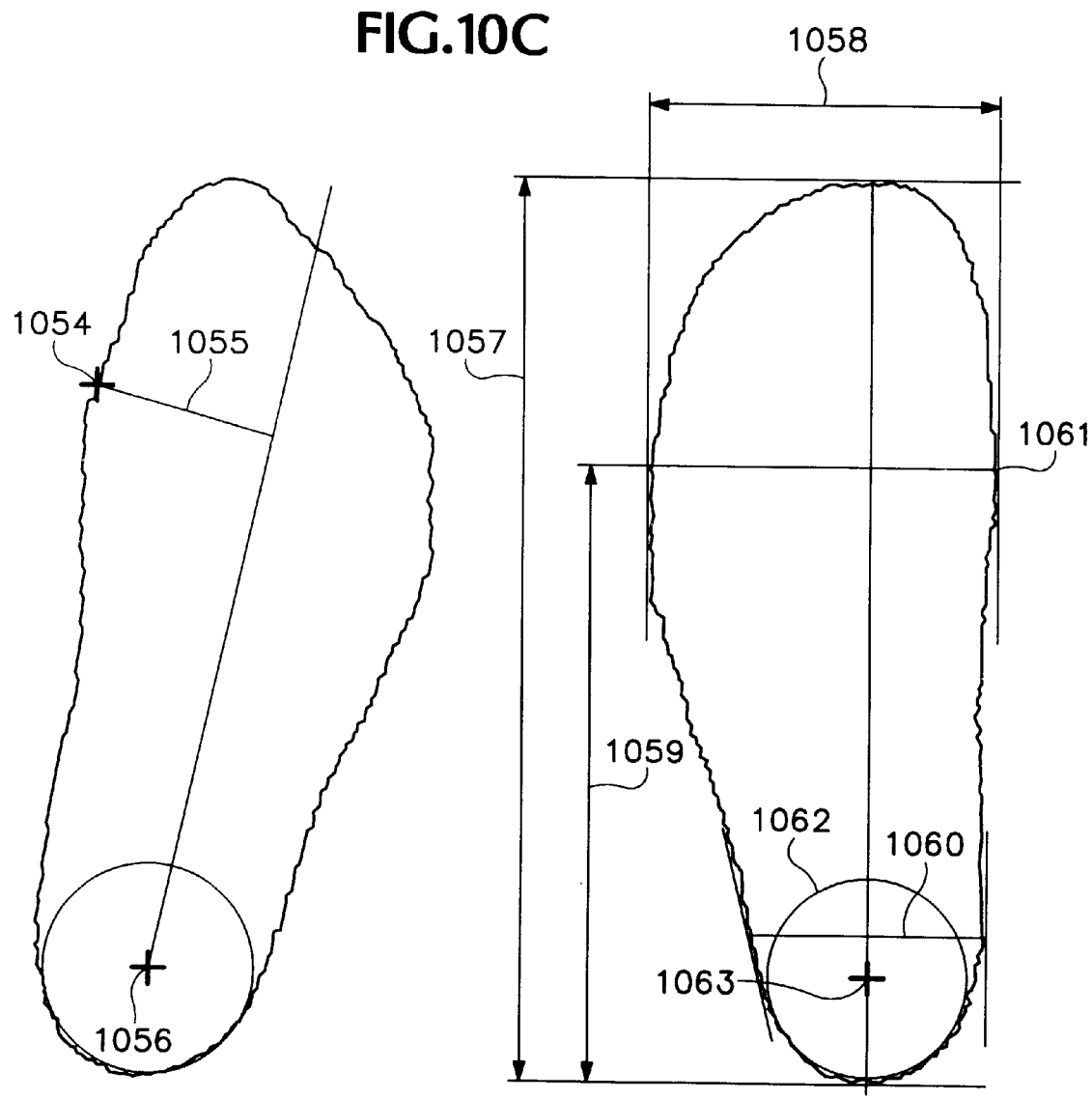
FIG. 10D illustrates graphically how an initial foot alignment procedure can be performed.
FIG. 10E shows various foot measurements which can be taken.

Referring again to FIG. 10A, key measurements are extracted beginning in step 1005. Now that the foot is in a standard alignment, the key measures can be determined. The measurements taken are as shown in FIG. 10E. The overall length (reference numeral 1057) can be obtained by taking the difference of minimum and maximum length values on the foot. The width (reference numeral 1058) can be measured from the first metatarsal head (already found) to the furthest width point found on the opposite side. The arch length (reference numeral 1059) can be obtained as the distance from the first metatarsal head to the back of the heel. The heel width (reference numeral 1060) is the distance at a preset location in front of the heel. The metatarsal head is indicated by reference numeral 1061; the heel circle is indicated by reference numeral 1062; and the heel center is indicated by reference numeral 1063.

Referring again to FIG. 6, contact area processing (step 614) will now be described, with particular reference to FIGS. 11A through 11D.

Figure 11A:
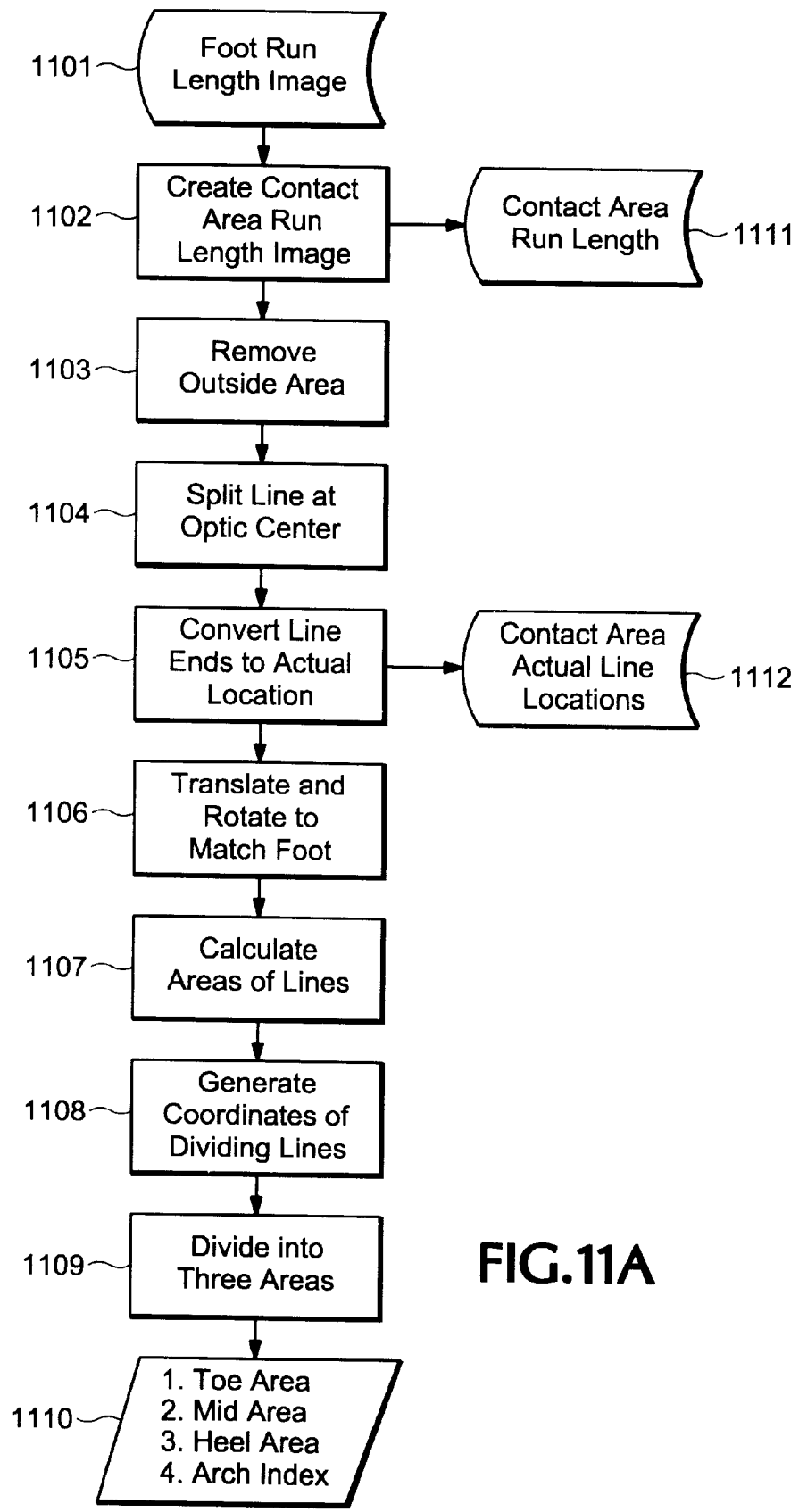
FIG. 11A shows steps which can be used to perform contact area processing (step 614 of FIG. 6).

The arch index is determined as follows. The inside black area in the foot object represents the actual contact area of the foot. This area can be used to generate the arch index, which is believed to be a reliable indicator of arch height. FIG. 11A shows a process for obtaining a ratio that can be correlated to arch index.

The arch index is ratio of the mid area to the total area (see FIG. 11B). As shown in FIG. 11B, a darkened contact area is indicated by reference numeral 1150; a toe area by reference numeral 1120; a mid area by reference numeral 1130; and a heel area by reference numeral 1140.

Referring again in FIG. 11A, processing begins in step 1102, where a contact area run length image is created from the foot run length image 1101. The contact area is obtained by going through each row in the run length image. Any length between the beginning and end of the foot contour not already contained in a run length is considered part of the contact area. In other words, any pixel which does not have a white value is deemed to be black.

Next, in step 1103, the outside area is removed. One problem is that there may be dark areas created on the outside of the foot. All dark objects are checked and any that are in contact with the outside contour are removed. As shown in FIG. 11C, a dark area 1160 will be removed, while the normal contact area 1170 will remain.

Figure 11D:
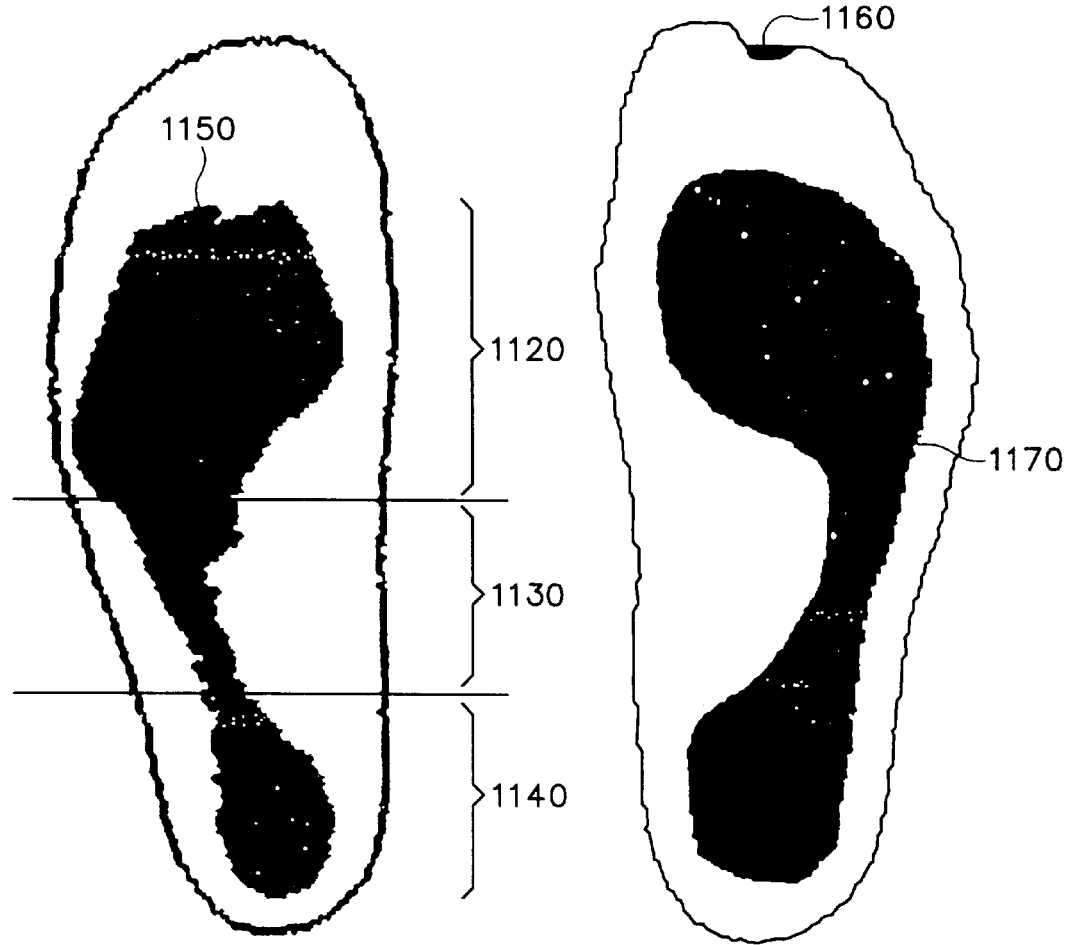
FIG. 11D shows splitting of run lengths at the optic center.
Figure 11D:
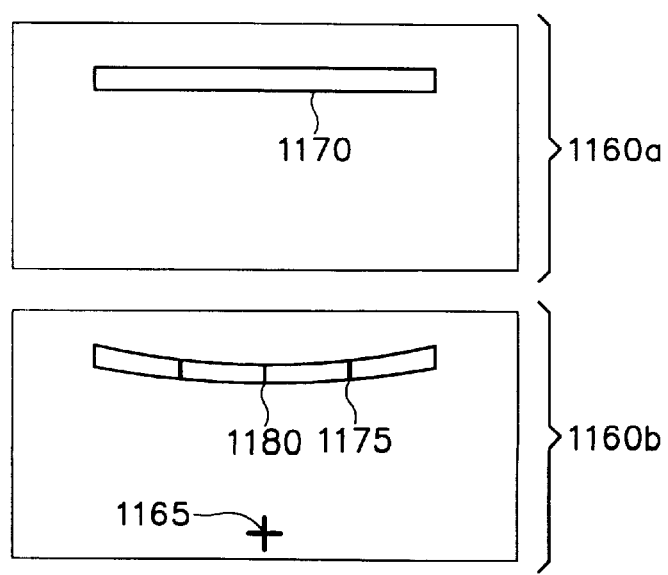

Next, in step 1104, all run lengths are "split" at the optic center (see FIG. 11D). The run lengths were obtained from the original camera view. The actual area of each row must be determined. However, the true shape is fairly complex. The center of the row is thinner than the two edges.

Referring briefly to FIG. 11D, reference numeral 1160*a* shows the camera image of a single line 1170, while reference numeral 1160*b* shows the actual shape of the same line. The first step taken to simplify the calculation is to split all run lengths crossing the optic center into two pieces. Reference numeral 1165 indicates the optic center, reference numeral 1175 indicates a midpoint used for an average width, and reference numeral 1180 indicates the split in the line. That is, the areas of the split run lengths are approximated by taking the width of the center and multiplying it by the length.

Referring again to FIG. 11A, in step 1105 the line ends are converted to actual locations. This step uses the same optical corrections shown in FIG. 9. The end points for the lines are translated into actual locations. Essentially, this step and step 1106 perform the same operations on the center contact area that was performed on the outside contour.

Step 1106 uses the same rotation described in FIG. 10D. The rotation is applied to the end points of the lines in the contact area. The translation and rotation was saved from step 1004.

In step 1107, the areas of the lines are calculated. The process used to calculate the area is shown in FIG. 11D. It is essentially an approximation based on determining the length of the two ends of the line and the width at the center.

In step 1108, the coordinates of dividing lines are generated. Referring briefly to FIG. 11B, the three areas 1120, 1130 and 1140 are divided by two lines. These two lines are drawn based on percentages of the overall contact area (1150 in FIG. 11B). One possible arrangement is to have the toe (1120)/mid areas (1130) divided at 57.4% of overall contact area length. The mid (1130)/heel areas (1140) can be divided at 28.9%. These percentages are derived based on experimental trials correlating to the traditional arch index.

Finally, in step 1109, the runs are separated into three areas with individual runs being divided based on the percentage of the area in each section.

The arch index (ratio of total contact area to mid area 1130) is a dimensionless quantity which relates to arch height (low arch index means a high arch). This quantity can help a customer select a shoe model that has the proper arch support, or to select an insert.

Figure 12A:
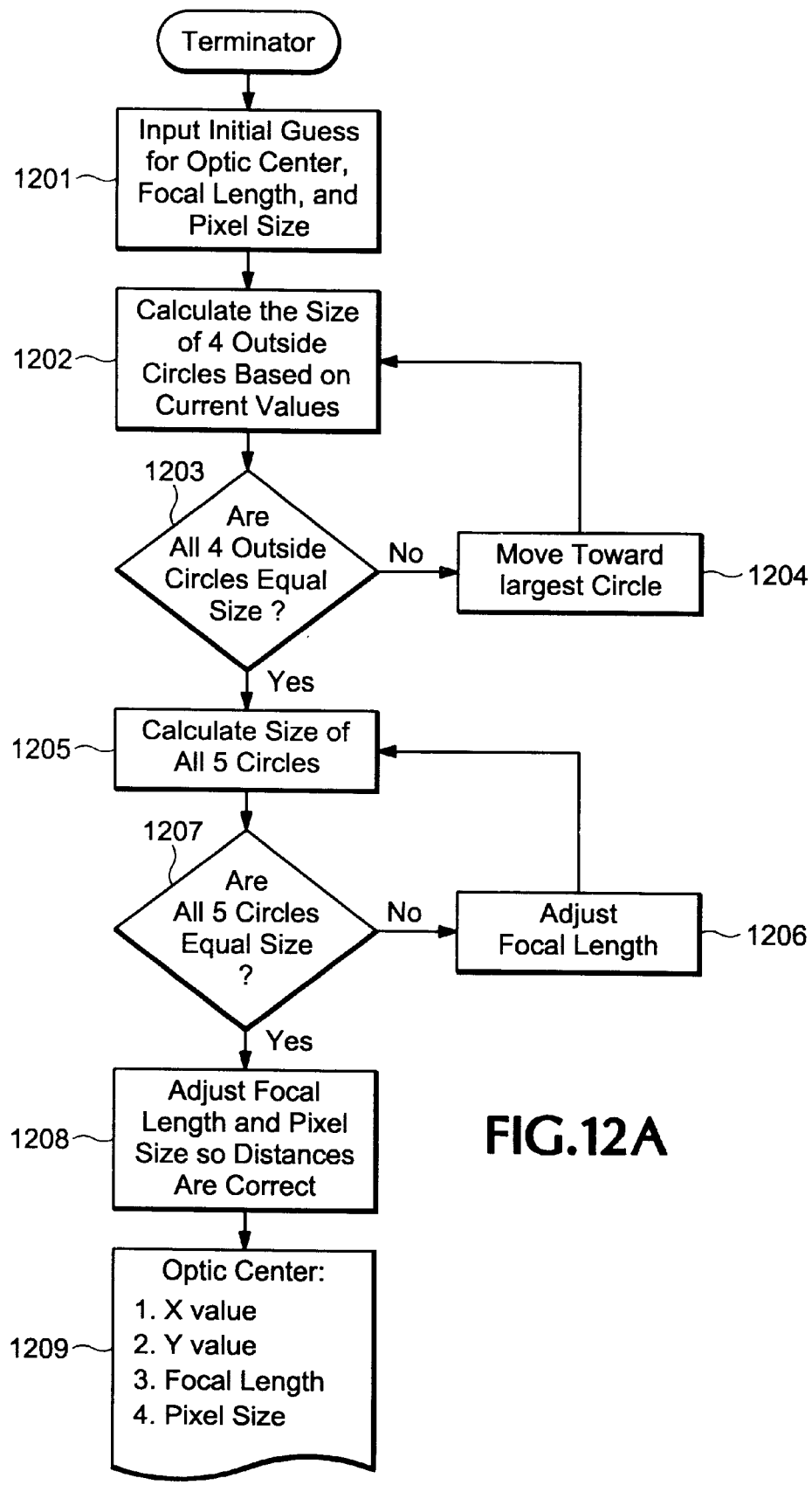
FIG. 12A shows various steps which may be used to calibrate a device incorporating various features of the invention.

FIGS. 12A and 12*b* show steps which may be used to calibrate a device in accordance with various aspects of the invention. The constants required to produce the optic distortion corrections (described in a previous section) are obtained from the calibration process. The goal of the calibration process is to obtain the following constants: (1) optic center (both X and Y values); (2) focal length; and (3) ratio of pixels to angles.

The initial step in the calibration process is to obtain in image of the calibration "target" shown in FIG. 12B. The target comprises of a piece of clear plastic having 5 holes of approximately 50 mm in diameter cut therein. Other shapes and sizes are of course possible.

Referring again to FIG. 12A, in step 1201 initial estimates of the optic center, focal length, and angle per pixel can be obtained from the original design of the optic systems (i.e., manually entered). The remaining calibration should only have to deal with variations in tolerances that can not be removed easily.

In step 1202, the size of the four outer circles of the calibration target (FIG. 12B) is calculated based on the initial estimates. The optic center is moved toward the largest calculated circle until all four outside circles are approximately the same size. In step 1203, a test is made to determine whether the calculated size of all 4 circles are equal. If not, then in step 1204 the optic center is moved toward the largest circle.

If, in step 1203, all 4 circles have the same calculated size, then in step 1205 the size of all 5 circles is calculated. Thereafter, in step 1207 a test is made to determine whether the size of all 5 circles is the same. If not, then in step 1206 the focal length is adjusted. If the sizes are the same, then in step 1208 the focal length and pixel sizes are adjusted so that the distances are correct.

The focal length parameter is adjusted using the center circle. If the center circle is smaller than the outer four, the local length value is decreased. Finally, both the angle to pixel ratio and focal length are adjusted together to make the target dimensions match the actual dimensions.

Figure 12C:
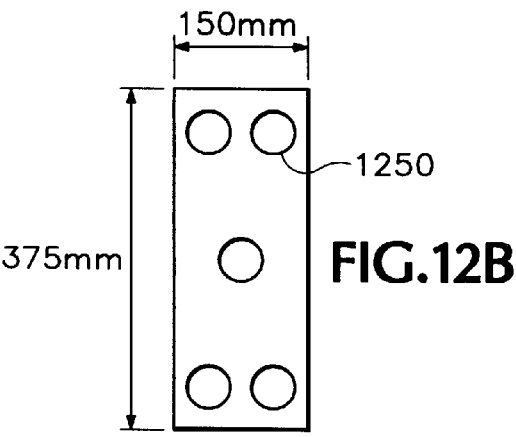
FIG. 12C shows graphically correction of optical center and focal length.
Figure 12C:
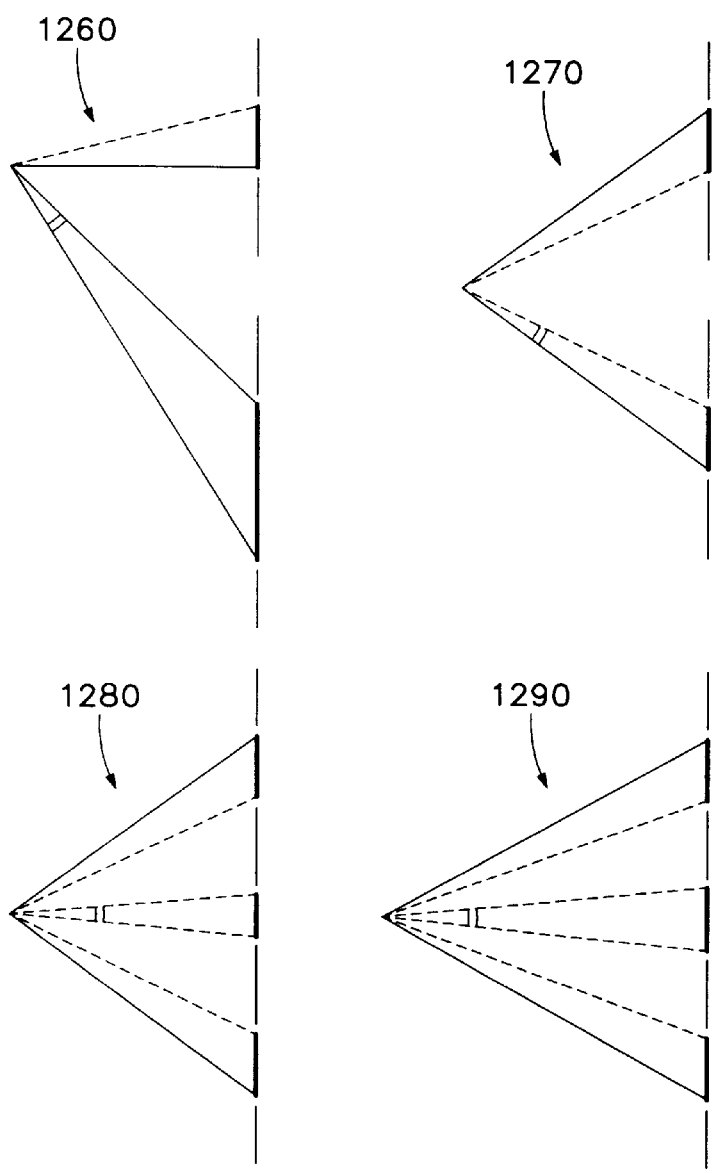

The top half of FIG. 12C shows correction of optical center. Changing the optical center changes the calculated size. In diagram 1260, the optical center is too high, resulting in a calculated size which is too large. Moving the optical center to the correct location produces two lines of the same length. In this case, the correct optical center is midway between the two lines (diagram 1270). Although FIG. 12C depicts only two dimensions, the actual calibration process occurs in three dimensions (i.e., two independent problems in X and Y and the analysis in the drawings applied independently to each axis).

The lower half of FIG. 12C shows the effect of changing the focal length. For simplicity, the optical center is correctly shown in the bottom half of FIG. 12C. If the trial focal length is too close, the calculated value for the center is too small. Increasing the focal length increases the calculated size. if the optical center has been correctly located, the outer four circles should all remain almost equal in size, independent of focal length.

Thus has been described an apparatus and method for inexpensively determining foot size information with a minimum of parts. The present invention can be used in many different applications beyond the automatic measurement of feet. As one example, the invention may be used to measure hands for biometric purposes or to determine clothing sizes such as for gloves.

It is apparent that many modifications and variations of the present invention are possible, and references to specific values are by example only. For example, although it is generally preferable to have the human extremity rest on the surface of the transparent plate, it will be recognized that placing the extremity in close proximity thereto would perform substantially the same function in substantially the same way and achieve substantially the same result.

Additionally, the method steps of the invention may be practiced in a different ordered sequence from that enumerated in the claims without departing from the scope of the invention. It is, therefore, to be understood that within the scope of the appended claims the invention may be practiced otherwise than as specifically described.

What is claimed is:

1. Apparatus for measuring a human extremity, comprising:

a housing including a transparent plate;

light projection means, arranged around the periphery of the transparent plate, for projecting light against substantially an entire periphery of a human extremity placed on a surface of the transparent plate; and image capture means, disposed to receive light reflected through the transparent plate from the periphery of a human extremity placed on the surface of the transparent plate, capture the reflected light, and store a digital representation of the reflected light.

2. The apparatus according to claim 1, wherein the light projection means projects light in the near-infrared wavelength range.

3. The apparatus according to claim 1, wherein the light projection means includes a plurality of light-emitting diodes that emit light at a wavelength of approximately 880 nanometers.

4. The apparatus according to claim 1, wherein the transparent plate includes a filter that blocks visible light but that passes near-infrared light.

5. The apparatus according to claim 1, wherein the image capture means includes a digital camera coupled to a frame grabber.

6. The apparatus according to claim 1, wherein the light projection means includes a computer-controlled illumination control circuit that alternately illuminates and darkens a human extremity placed on the surface of the transparent plate in conjunction with successive images of reflected light captured by the image capture means.

7. The apparatus according to claim 1, wherein the image capture means includes a near-infrared spectral filter which approximately matches the wavelength of light emitted by the light projection means.

8. The apparatus according to claim 1, wherein the transparent plate includes an aspheric Fresnel lens.

9. The apparatus according to claim 1, further including a computer, coupled to the light projection means and the image capture means, for controlling the light projection means to alternately darken and lighten substantially the entire periphery of a human extremity placed on the surface of the transparent plate, and controlling the image capture means to store both a dark and a light image of a human extremity placed on the surface of the transparent plate.

10. The apparatus according to claim 1 wherein the light projection means is arranged so as not to project light against portions of the extremity that are in contact with the transparent plate.

11. Apparatus for measuring a human extremity, comprising:
a housing including a transparent plate;
a plurality of optical illuminators, arranged around a periphery of the transparent plate, for generating and projecting light against substantially an entire periphery of a human extremity placed on a surface of the transparent plate;
a digital camera, disposed within the housing and arranged to
receive light reflected through the transparent plate from substantially an entire periphery of a human extremity placed on the surface of the transparent plate,
capture the reflected light, and
store a dipital representation of the reflected light.

12. The apparatus of claim 11, wherein the plurality of optical illuminators project light in the near-infrared range.

13. The apparatus of claim 12, wherein each optical illuminator includes a light-emitting diode a cylinder lens disposed along an optical path of the light emitting diode, and a mirror disposed along the optical path of the light emitting diode that reflects light from the cylinder lens onto substantially an entire periphery of a human extremity placed on the surface of the transparent plate.

14. The apparatus of claim 11, wherein the transparent plate includes an aspheric Fresnel lens.

15. The apparatus of claim 14, wherein the transparent plate further includes a filter that blocks visible light but transmits light in the near-infrared range.

16. The apparatus of claim 11, wherein each optical illuminator includes a light-emitting diode having an emitter structure that produces a beam with a small angular divergence and without a dark spot.

17. The apparatus of claim 11, further including a computer having a frame grabber coupled to the digital camera and an illumination control circuit coupled to the plurality of optical illuminators, the computer being programmed to selectively control the frame grabber and illumination control circuit in order to obtain both illuminated and non-illuminated images of a human extremity placed on the surface of the transparent plate.

18. The apparatus of claim 17, wherein the computer is further programmed to
subtract the illuminated images from the non-illuminated images to obtain subtracted images,
perform a low-pass filtering operation on the subtracted images to obtain low-pass filtered images, and
perform a thresholding operation on the low-pass filtered images.

19. The apparatus of claim 18, wherein the computer is further programmed to generate an outer contour of a human extremity placed on the surface of the transparent plate by producing a run-length data structure from the result of the thresholding operation.

20. The apparatus of claim 17, wherein the computer is further programmed to generate an arch length from the illuminated and non-illuminated images.

21. The apparatus of claim 17, wherein the computer is further programmed to correct for optical distortion based on correction factors determined with respect to a previously performed calibration process.

22. The apparatus of claim 11 wherein the optical illuminators are arranged so as not to project light against portions of the extremity that are in contact with the transparent plate.

23. The apparatus of claim 11, further including a mirror, disposed within the housing along an optical path between the transparent plate and the digital camera, for directing the reflected light toward the digital camera.

24. A system for capturing information about the shape of an object, comprising:
a housing including a transparent plate;
an optical illuminator, arranged around the periphery of the transparent plate, for generating and projecting light against substantially an entire periphery of an object resting on a surface of the transparent plate;
a camera within the housing disposed to
receive light reflected through the transparent plate from substantially an entire periphery of an object resting on the surface of the transparent plate,
capture the reflected light, and
generate a digital representation of the captured reflected light;
a frame grabber, coupled to the camera, for receiving and storing into a memory the digital representation of the captured digital representation generated by the camera;
an illuminator control circuit, coupled to the optical illuminator, for switching the optical illuminator on and off; and
a computer coupled to the frame grabber and programmed to store, from the frame grabber, both an illuminated image of the object produced from a digital representation of reflected light that is captured when the optical illuminator is switched on and a non-illuminated image of the object produced from a digital representation of reflected light that is captured when the optical illuminator is switched off.

25. The system of claim 24, wherein the computer
is coupled to the illuminator control circuit, and
is further programmed to command the illuminator control circuit to switch the optical illuminator on and off.

26. The system of claim 24, wherein the optical illuminator projects light in the near-infrared range, and wherein the camera is filtered to receive light in the near-infrared range.

27. The system of claim 24, wherein the transparent plate includes:
a clear surface which transmits visible light;
a first filter, adjacent to the clear surface, which transmits light in a first range of wavelengths; and
a second filter, adjacent to the first filter, which transmits lights in a second range of wavelengths that is different from the first range of wavelengths.

28. The system of claim 24, wherein the transparent plate includes:
a first surface including a material selected from the set consisting of glass and plastic; and
an aspherical Fresnel lens adjacent to the first surface.

29. The system of claim 24, wherein the computer is further programmed to
subtract the illuminated and non-illiuninated images to produce a subtraction image, filter the subtraction image to generate a low-pass filtered image, and threshold the low-pass filtered image.

30. The system of claim 29, wherein the computer is further programmed to generate an outside contour of the object resting on the surface of the transparent plate from a run-length encoding of the low-pass filtered image.

31. The system of claim 29, wherein the computer is further programmed to isolate an image of human extremity from other information in the low-pass filtered image, and further to determine whether the isolated image represents a left or a right extremity.

32. The system of claim 31, wherein the computer is further programmed to generate size information for the human extremity based on the low-pass filtered image, the size information including length, width, and an arch index.

33. The system of claim 24, wherein the housing, transparent plate and camera are arranged such that the distance of an optical path from the camera to the transparent plate is approximately 12 inches.

34. The system of claim 24 wherein the optical illuminator is arranged so as not to project light against portions of the object that are in contact with the transparent plate.

35. A method of capturing an image of a human extremity, comprising the steps of:
   (1) placing the human extremity on a transparent plate;
   (2) projecting light onto substantially the entire periphery of the human extremity while the human extremity is placed on the surface of the transparent plate; and
   (3) capturing in a camera an image of the light reflected by the periphery of the human extremity through the transparent plate and storing the captured image into a digital memory.

36. The method of claim 35, wherein step (2) includes the step of projecting near-infrated wavelength light, and wherein step (3) includes the step of filtering the reflected light to near-infrared wavelength light.

37. The method of claim 35, wherein step (1) includes the step of placing a human foot on the transparent plate, and wherein step (2) includes the step of projecting light having a wavelength of approximately 880 nanometers.

38. The method of claim 35, wherein step (2) includes the step of alternately activating and de-activating optical illuminators to produce illuminated and non-illuminated images of the light reflected by the human extremity, and wherein step (3) includes the step of capturing in the camera both the illuminated and non-illuminated images.

39. A method for capturing an image of a human extremity, comprising the steps of:
   (1) placing the human extremity on a transparent plate;
   (2) projecting light onto the periphery of the human extremity, but not onto portions of the human extremity that are in contact with the transparent plate; and
   (3) capturing in a camera an image of the light reflected by the human extremity through the transparent plate, and storing the captured image.

40. A method for capturing an image of a human extremity, comprising the steps of:
   (1) placing the human extremity on a transparent plate;
   (2) projecting light for a finte period onto the periphery of the human extremity while placed on the surface of the transparent plate by activating and then deactivating optical illuminators; and
   (3) capturing in a camera both the illluminated image of the human extremity as seen through the transparent plate when the optical illuminators are activated and the non-illuminated image of the human extremity as seen through the transparent plate when the optical illuminators are deactivated.

41. The method of claim 40, further including the step of:
   (4) subtracting the illuminated and non-illuminated images in a computer to produce a subtracted image for which ambient light effects have been substantially removed.

42. The method of claim 41, further including the steps of:
   (5) low-pass filtering the subtracted image; and
   (6) thresholding the low-pass filtered image.

43. The method of claim 42, further including the steps of:
   (7) encoding the low-pass filtered image using a run-length encoding scheme; and
   (8) separating out an image of the human extremity from the run-length encoded image.

44. The method of claim 43, further including the steps of:
   (9) generating an outer contour of the human extremity from the result of step (8); and
   (10) calculating a length and width of the human extremity based on the outer contour created in step (9).

45. The method of claim 41, further including the step of correcting for optical distortion using correction factors determined with respect to a previously performed calibration process.

46. The method of claim 41, further including the step of determining a contact area of the human extremity on the transparent plate.

47. The method of claim 40, further comprising the step of:
   (4) subtracting the illuminated and non-illuminated images in a computer to produce a subtracted image which ambient light effects have been substantially removed.

* * * * *